(12) United States Patent
    Morefield

(10) Patent No.: US 9,603,918 B2
(45) Date of Patent: Mar. 28, 2017

(54) VACCINE FORMULATION

(71) Applicant: Garry Lee Morefield, Nazareth, PA (US)

(72) Inventor: Garry Lee Morefield, Nazareth, PA (US)

(73) Assignee: VAXFORM LLC, Bethlehem, PA (US)

( * ) Notice: Subject to any disclaimer, the term of this patent is extended or adjusted under 35 U.S.C. 154(b) by 0 days.

(21) Appl. No.: 14/544,577

(22) Filed: Jan. 23, 2015

(65) Prior Publication Data

US 2016/0213769 A1  Jul. 28, 2016

(51) Int. Cl.
    *A61K 39/09* (2006.01)
    *A61K 9/16* (2006.01)
    *A61K 39/00* (2006.01)

(52) U.S. Cl.
    CPC .......... *A61K 39/092* (2013.01); *A61K 9/1623* (2013.01); *A61K 9/1694* (2013.01); *A61K 2039/55505* (2013.01)

(58) Field of Classification Search
    None
    See application file for complete search history.

(56) References Cited

U.S. PATENT DOCUMENTS

| | | | |
|---|---|---|---|
| 6,399,332 B1 | 6/2002 | Ulrich et al. | |
| 6,713,284 B2 | 3/2004 | Ulrich et al. | |
| 7,087,235 B2 | 8/2006 | Ulrich et al. | |
| 7,378,257 B2 | 5/2008 | Ulrich et al. | |
| 7,750,132 B2 | 7/2010 | Ulrich et al. | |
| 8,067,202 B2 | 11/2011 | Ulrich et al. | |
| 8,710,185 B2 | 4/2014 | Ulrich et al. | |

OTHER PUBLICATIONS

Ulrich RG. J. Immune Based Ther. Vaccines 6: 1-8, 2008.*
Callahan P. M., et al., The importance of surface charge in optimization of antigen-adjuvant interactions, Pharmaceutical Research 8(7):851-858 (1991).
Exley C., et al., The immunobiology of aluminium adjuvants: how do they really work?, Trends in Immunology 31:103-109 (2010).
Harris J., et al., The role of inflammasomes in the immunostimulatory effects of particulate adjuvants, Eur. J. Immunology 40:595-65 (2010).
Marrack P., et al., Towards an understanding of the adjuvant action of aluminium, Nature Reviews Immunology 9:287-293 (2009).

* cited by examiner

*Primary Examiner* — S. Devi
(74) *Attorney, Agent, or Firm* — Prince Lobel Tye LLP; Thomas J. Bordner

(57) ABSTRACT

The present invention relates to immunological compositions and vaccines that target diseases caused by infection with *Streptococcus pyogenes*. In particular, the compositions of the present invention find use in therapeutic and/or prophylactic methods for the treatment or prevention of morbidity associated with infection with *Streptococcus pyogenes*. The present invention also relates to methods of making the immunological compositions and vaccines as well as methods for producing stable SpeAB antigen formulations in combination with one or more additional immunologically active substituents (e.g., adjuvants).

6 Claims, 11 Drawing Sheets

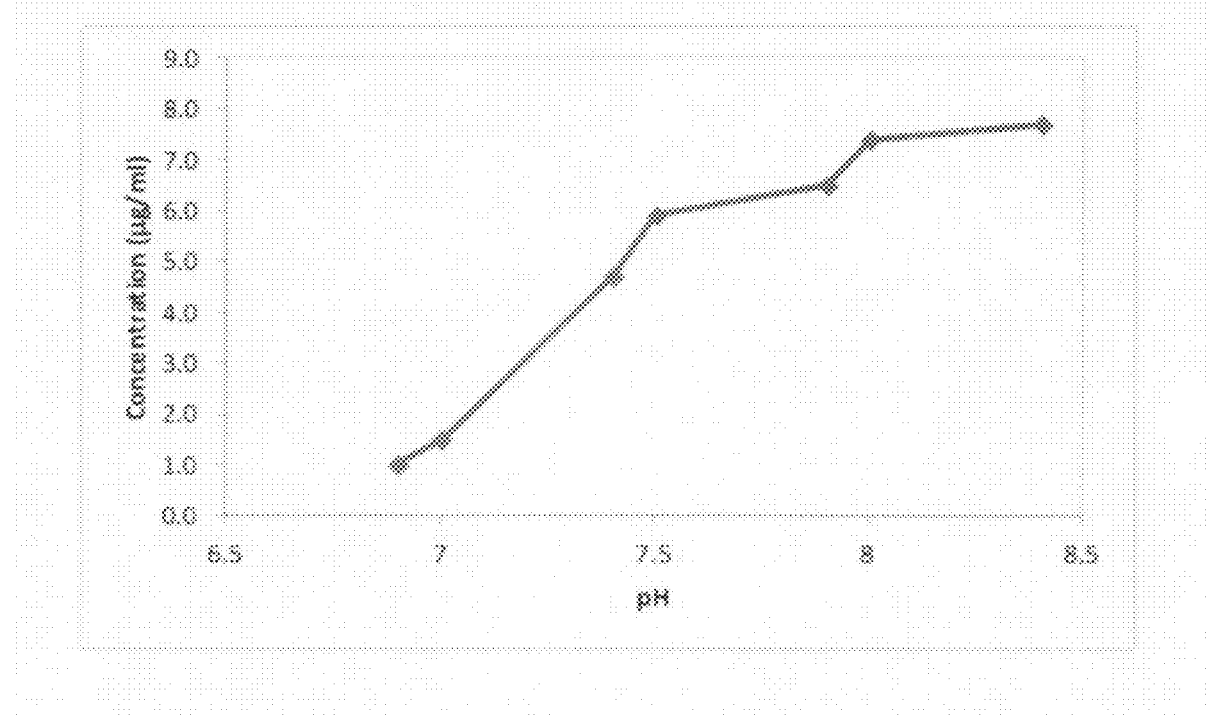

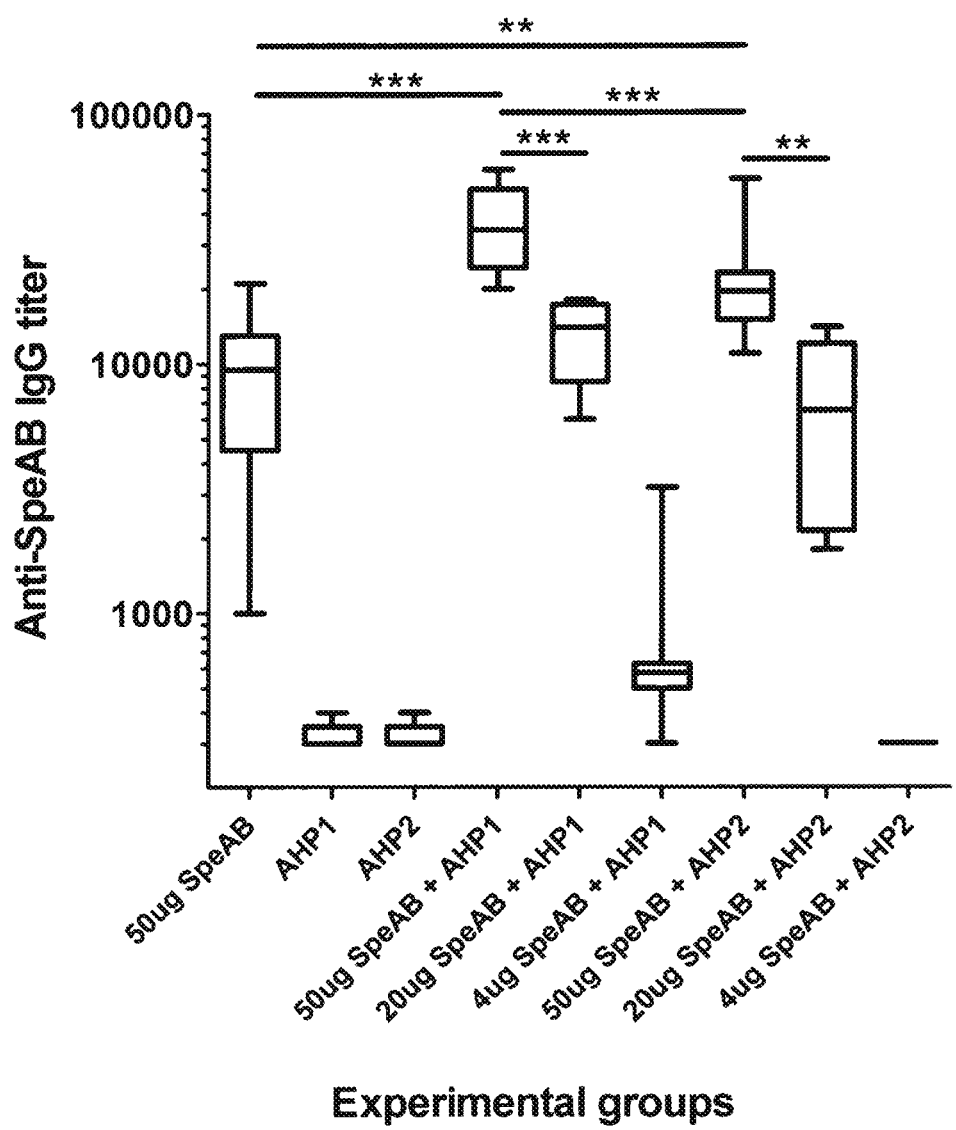

VACCINE FORMULATION

FIELD OF THE INVENTION

The present invention relates to immunological compositions and vaccines that target diseases caused by infection with *Streptococcus pyogenes*. In particular, the compositions of the present invention find use in therapeutic and/or prophylactic methods for the treatment or prevention of morbidity associated with infection with *Streptococcus pyogenes*. The present invention also relates to methods of making the immunological compositions and vaccines as well as methods for producing stable SpeAB antigen formulations in combination with one or more additional immunologically active substituents (e.g., adjuvants).

BACKGROUND OF THE INVENTION

*Streptococcus pyogenes* (*S. pyogenes*) is a Gram-positive beta-hemolytic bacterium classified in Lancefield serogroup A (commonly known as group A streptococci). *S. pyogenes* is the cause of many important human diseases, ranging from mild superficial throat (e.g., pharyngitis) and skin infections (e.g., impetigo) to life-threatening systemic diseases. Infections typically begin in the throat or skin. *S. pyogenes* is the most common bacterial cause of acute pharyngitis in children (15-30% of pediatric cases) and adults (5-10% of adult cases). The economic burden for treating pharyngitis is substantial. The medical costs associated with just treating pharyngitis in children in the United States alone reaches an estimated 540 million dollars per year. In addition to being a common etiological agent of upper respiratory tract and skin infections, *S. pyogenes* also causes certain invasive systemic infections. Nevertheless, asymptomatic infection and carriage are also common features of *S. pyogenes* infection.

Importantly, *S. pyogenes* is an infrequent but usually pathogenic part of skin flora in humans that is responsible for, or implicated in, a wide variety of diseases and morbidities. These diseases are generally referred to as Group A Streptococcal (GAS) diseases. GAS diseases include a diverse variety of suppurative aliments and nonsuppurative postinfectious sequelae. Suppurative GAS diseases are known to include pharyngitis (e.g., tonsillopharyngeal cellulitis or abscess), impetigo, pneumonia, necrotizing fasciitis, cellulitis, Streptococcal bacteremia, osteomyelitis, otitis media, scarlet fever, sinusitis, and even meningitis or brain abscess can occur as sever but fortunately rare complications of ear or sinus infections. In turn, nonsuppurative sequelae of GAS infections include acute rheumatic fever (ARF) (as defined by the Jones criteria), rheumatic heart disease, and acute glomerulonephritis. *S. pyogenes* is also a known cause of toxic shock syndrome (TSS).

Military units have long recognized the importance of *S. pyogenes* infections and of GAS disease as major burdens on unit readiness and effectiveness. *S. pyogenes* was one of the first pathogens specifically identified as a causative bacterial agent of considerable morbidity in massed troops. During World War II, scarlet fever, a GAS disease, was responsible for more than 1.3 million lost workdays in the United States Army. More than 1,600 cases of recognized streptococcal illness were documented for every 108 cases of malaria and one (1) case of polio. The highest incidence of streptococcal illness was among recruits. Unlike malaria and polio, in which symptomatic individuals would likely seek medical attention, infected recruits typically failed to report their illness or to seek medical attention further exacerbating the spread of GAS disease related issues within military units.

A number of factors make prevention of *S. pyogenes* caused illness difficult, in both the military and civilian populations, these factors include, asymptomatic carriage of *S. pyogenes*, prolonged bacterial shedding following symptomatic illness, and the potential for direct transmission to uninfected individuals. A vaccine for the prevention of *S. pyogenes* infection would be beneficial not only for the military but would also have a tremendous impact on improving health in civilian populations.

In the United States, there are an estimated 10 million cases of non-invasive GAS disease and between 9,000-11,500 cases of invasive disease annually. (hypertext transfer protocol://www.cdc.gov/ncidod/dbmd/diseaseinfo/groupastreptococcal_t.htm). GAS Disease resulting from invasive infection can have mortality rates as high as 35%. Indeed, an estimated 500,000 deaths worldwide are attributed to *S. pyogenes* infections each year. (hypertext transfer protocol://www.who.int/child_adolescent health/documents/ivb_05_14/en/, 2005). Although the overall incidence of total GAS disease related deaths are low, the mortality rate among cases of streptococcal toxic shock-like syndrome is relatively high at about 45%. Additionally, there is growing evidence for the role of GAS infection in the causation of pediatric autoimmune neuropsychiatric disorders (PANDAS).

While GAS infections can generally be successfully treated with antibiotics these treatments cannot guarantee prevention of complications (e.g., pediatric glomerulonephritis) associated with the underlying infection. Reliance on the use of antibiotics can result in antibiotic resistant strains arising in a population. Indeed, antibiotic resistant strains of *S. pyogenes* have recently emerged and have thusly become an additional concern in combating GAS diseases.

Due to the wide range of morbidities associated with *S. pyogenes* infection, the potential for outbreaks of antibiotic resistant *S. pyogenes* infections, and the correspondingly high medical costs for treating GAS infections as well as the lost productivity and, more importantly, potential for human deaths sometimes resulting from GAS diseases an effective vaccine against *S. pyogenes* is needed both in the ranks of the military as well as in civilian populations. An effective vaccine could save thousands of lives and allow for billions of dollars of medical expenditures to be saved by reducing the number of *S. pyogenes* infection and/or GAS associated diseases.

SUMMARY OF THE INVENTION

The present invention relates to immunological compositions and vaccines that target diseases caused by infection with *Streptococcus pyogenes*. In particular, the compositions of the present invention find use in therapeutic and/or prophylactic methods for the treatment or prevention of morbidity associated with infection with *Streptococcus pyogenes*. The present invention also relates to methods of making the immunological compositions and vaccines as well as methods for producing stable SpeAB antigen formulations in combination with one or more additional immunologically active substituents (e.g., adjuvants).

Diseases resulting from infection by group A *streptococcus* are an increasing burden on global health. The present invention provides novel immunogenic formulations, therapeutic formulations, and prophylactic vaccines developed to treat, prevent, and/or ameliorate *S. pyogenes* infections and GAS associated diseases. In preferred embodiments, formulations (e.g., vaccines) incorporate recombinant fusion protein antigens (e.g., SpeAB) that are engineered by combining inactive and/or mutant forms of streptococcal pyrogenic exotoxin A (SpeA) and streptococcal pyrogenic exotoxin B (SpeB) from the organism *S. pyogenes*. In particular, various forms of native, recombinant, and/or mutant SpeA, SpeB and/or SpeAB antigens as well as antigens (and/or immunogens) from related superantigens, including, but not limited to, staphylococcal entertoxins A-E, toxic shock syndrome toxin-1 (TSST-1), and generally streptococcal pyrogenic exotoxins A, B, and C, in addition to antigens as described in U.S. Pat. No. 7,750,132; U.S. Pat. No. 7,087,235; U.S. Pat. No. 6,713,284; and U.S. Pat. No. 6,399,332 (each of which is hereby incorporated by reference in its entirety) are incorporated into various compositions and methods of the present invention. In preferred embodiments, the present invention provides recombinant SpeAB immunological compositions or vaccines that provide protection against, or lessen the effects of, diseases caused by various serotypes of *S. pyogenes*.

An immunogen for use in the vaccines and methods of the invention may be selected from the group consisting of virus, bacteria, parasite, protozoan, and fungus, products derived from the virus, bacteria, parasite, protozoan, and fungus, a cancer antigen, a degenerative disease antigen, an atopic disease antigen, an autoimmune disease antigen, an alloantigen, a xenoantigen, a metabolic disease enzyme or enzymatic product, a recombinantly produced protein or peptide, a chimeric fusion protein, and a small molecule. In one embodiment, the at least one immunogen is a component of a commercially available vaccine. In one embodiment, the immunological compositions and/or vaccines of the present invention comprise at least one adjuvant. In one embodiment, the at least one of the adjuvants is a metallic adjuvant such as alum.

In one embodiment, one or more viral immunogens are selected from the group comprising, but not limited to, pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, and/or hepatitis E virus.

In one embodiment, one or more bacterial immunogens are selected from (e.g., obtained from) organisms in group comprising, but not limited to, *Borrelia* species, *Bacillus anthracis, Borrelia burgdorferi, Bordetella pertussis, Camphylobacter jejuni, Chlamydia* species, *Chlamydial psittaci, Chlamydial trachomatis, Clostridium* species, *Clostridium tetani, Clostridium botulinum, Clostridium perfringens, Corynebacterium diphtheriae, Coxiella* species, an *Enterococcus* species, *Erlichia* species, *Escherichia coli, Francisella tularensis, Haemophilus* species, *Haemophilus influenzae, Haemophilus parainfluenzae, Lactobacillus* species, a *Legionella* species, *Legionella pneumophila, Leptospirosis interrogans, Listeria* species, *Listeria monocytogenes, Mycobacterium* species, *Mycobacterium tuberculosis, Mycobacterium leprae, Mycoplasma* species, *Mycoplasma pneumoniae, Neisseria* species, *Neisseria meningitidis, Neisseria gonorrhoeae, Pneumococcus* species, *Pseudomonas* species, *Pseudomonas aeruginosa, Salmonella* species, *Salmonella typhi, Salmonella enterica, Rickettsia* species, *Rickettsia ricketsii, Rickettsia typhi, Shigella* species, *Staphylococcus* species, *Staphylococcus aureus, Streptococcus* species, *Streptococccus pneumoniae, Streptococcus pyrogenes, Streptococcus mutans, Treponema* species, *Treponema pallidum*, a *Vibrio* species, *Vibrio cholerae*, and/or *Yersinia pestis*.

In one embodiment, one or more fungal immunogens are selected from (e.g., obtained from) organisms in group comprising, but not limited to, *Aspergillus* species, *Candida* species, *Candida albicans, Candida tropicalis, Cryptococcus* species, *Cryptococcus neoformans, Entamoeba histolytica, Histoplasma capsulatum, Leishmania* species, *Nocardia asteroides, Plasmodium falciparum, Toxoplasma gondii, Trichomonas vaginalis, Toxoplasma* species, *Trypanosoma brucei, Schistosoma mansoni, Fusarium* species, and/or *Trichophyton* species.

In one embodiment, one or more parasitical immunogens are selected from (e.g., obtained from) organisms in group comprising, but not limited to, *Plasmodium* species, *Toxoplasma* species, *Entamoeba* species, *Babesia* species, *Trypanosoma* species, *Leshmania* species, *Pneumocystis* species, *Trichomonas* species, *Giardia* species, and/or *Schisostoma* species.

In one embodiment, the protozic immunogens are selected from (e.g., obtained from) organisms in group comprising, but not limited to, *Cryptosporidium* species, *Plasmodium* species, *Entamoeba* species, *Naegleria* species, *Acanthamoeba* species, *Balamuthia* species, *Toxoplasma* species, *Giardia* species, *Trichomonas* species, *Leishmania* species, and/or *Trypanosoma* species.

In one embodiment, a suitable immunogen for use in the immunological compositions and/or vaccines and methods of the present invention is an alloantigen (a self-antigen), such as a protein or peptide, lipoprotein, lipid, carbohydrate, a nucleic acid, an enzyme, a structural protein, a secreted protein, a cell surface receptor, and/or a cytokine. In one embodiment, the self-antigen is an autoimmune disease antigen.

In addition to one or more common vaccinal antigens and/or superantigen family antigens (e.g., SpeAB), certain compositions further comprise one or more stabilizers such as: 1) amino acids, including, but not limited to, arginine, aspartate, glycine, glutamate, lysine, and proline; 2) antioxidants, including, but not limited to, ascorbic acid, EDTA, and malic acid; 3) cyclodextrins, including, but not limited to, $\alpha$ or $\beta$ cyclodextrin or derivitized cyclodextrins such as $\gamma$-hydroxypropyl-cyclodextrin; 4) proteins, including, but not limited to, albumin, and gelatin; 5) sugar/sugar alcohols, including, but not limited to, sucrose, trehalose, lactose dextrose, sorbital, and mannitol; and 6) surfactants, including, but not limited to, Brij, Tween, and Pluronic. Stabilizers in the present compositions enhance the stability of the various antigens presented. Within the meaning of the invention, enhanced stability relates to an improvement in the thermo stability of one or more of the included antigens (and/or immunogens) to resist temperature dependent denaturation. Similarly, in another meaning, enhanced stability relates to improved resistance of one or more of the included antigens to resist elevated temperature, chemical or otherwise induced (i.e., irradiation via electromagnetic spectrum) degradation or denaturation. In each of these meanings, enhanced stability is measured relative to a baseline stability as established for the particular antigens upon expose to or contact with a denaturing environment in a composition formulated without the stabilizer. In certain preferred embodiments, the compositions include sucrose and/or mannitol as stabilizes for the superantigen family antigen(s) in the composition such as SpeA, SpeB, and/or SpeAB antigens.

The present compositions can optionally further incorporate one or more adjuvants. There are a number of classes of adjuvants or types of adjuvants suitable for formulation in the present compositions. Adjuvants can be classified according to their source (natural, synthetic or endogenous), mechanism of action, or physical or chemical properties. Classes of adjuvants include but, are not limited to, those such as: 1) mineral salts (e.g., aluminum hydroxide, aluminum or calcium phosphate); 2) oil, oil-in-water emulsions, water-in-oil emulsions, and surfactant based formulations (e.g., MF59), QS21 (purified saponin), AS02 [SBAS2] (oil-in-water emulsion+MPL+QS-21), Montanide ISA-51 and ISA-720 (stabilized water-in-oil emulsion); 3) particulate adjuvants (e.g., virosomes, virus like particles, unilamellar liposomal vehicles incorporating influenza haemagglutinin), AS04 ([SBAS4] Al salt with MPL), ISCOMS (structured complex of saponins and lipids), polylactide co-glycolide (PLG); 4) microbial or bacterial derivatives natural and synthetic, (e.g., monophosphoryl lipid A, monophosphoryl lipid A+M. Phlei cell wall skeleton), AGP [RC-529] (synthetic acylated monosaccharide), DCChol (lipoidal formulations), OM-174 (lipid A derivative), CpG motifs (synthetic oligonucleotides), modified LT and CT (genetically modified bacterial toxins), C-type-lectin receptor agonists, and Toll-like receptor agonists; 5) endogenous immunostimulatory adjuvants (e.g., cytokines), endogenous human immunomodulators (e.g., hGM-CSF or hIL-12), and C3d tandem arrays; 6) plant derivatives (e.g., saponins, such as QS-21); and 7) inert vehicles and nanoparticles (e.g., gold particles/nanoparticles). Adjuvants are selected for their ability potentiate (e.g., enhance, accelerate, or prolong) or immunomodulate (e.g., modify the nature of response) the immune response in a subject in response to administration of an antigen or immunogen.

In certain embodiments, the compositions comprise mineral salt adjuvants. Preferably, the mineral salt adjuvants comprise aluminum adjuvants, and more preferably aluminum hydroxides (e.g., crystalline aluminum oxyhydroxide (AlO(OH)) and/or aluminum phosphates (e.g., amorphous aluminum hydroxyphosphates, and/or orthophosphates) of varying phosphate content, and/or aluminum sulfates, and/or mixtures thereof. Depending on numerous factors, but also on the phosphorylation status of the antigen, the antigen becomes more or less adsorbed onto the adjuvant. The antigens can be partially (e.g., <1 to 99%) or completely (e.g., >99%) adsorbed to the adjuvant or formulated so as to remain in solution.

The present invention relates to immunological compositions (e.g., vaccines) comprising one or more antigens including SpeA, SpeB and/or SpeAB antigens, aluminum (e.g., mineral adjuvant), phosphate, and a stabilizer.

In a preferred embodiments of the present invention, the compositions comprise SpeA, SpeB, and/or SpeAB antigens formulated as to be stabilized with a sugar (e.g., sucrose) or a sugar alcohol (e.g., mannitol), in which the antigen remains substantially adsorbed (i.e., >50%, 60%, 70%, 80%, 90%, or >99%, and values therein) to the aluminum adjuvant.

In another preferred embodiment, the composition comprises an immunological composition of SpeAB antigens formulated to be stabilized with sucrose, in which the antigen remains substantially adsorbed (i.e., >50%, 60%, 70%, 80%, 90%, or >99%, and values therein) to the aluminum adjuvant and phosphate.

In particularly preferred embodiment, the composition comprises a vaccine comprised of SpeAB antigens formulated to be stabilized with sucrose, in which the antigen remains substantially adsorbed (i.e., >50%, 60%, 70%, 80%, 90%, or >99%, and values therein) to the aluminum adjuvant and phosphate.

In addition to the aforementioned embodiments, the present invention relates to a number of additional compositions (immunological compositions and/or vaccines) including, but not limited to, the following embodiments.

The present invention relates to immunological compositions in which the SpeAB antigen is present in a concentration of between about 0.01, to about 1, to about 5, to about 20, to about 100 μg/ml and ranges and concentration values therein.

The present invention further relates to immunological compositions in which concentration of aluminum is between about 0.5 to about 1.7 mg/mland ranges and concentrations therein.

The present invention relates to immunological compositions in which the ratio of phosphate to aluminum is between about 0.025:1 to about 1:1 and ranges and concentrations therein.

The present invention relates to immunological compositions and/or vaccines comprising a stabilizer wherein the stabilizer is sucrose and/or mannitol.

The present invention relates to immunological compositions in which the stabilizer is present in an amount of from about 2 to about 20% wt/wt of the immunological composition.

The present invention relates to immunological compositions in which the pH of the composition is from about 7.0 to about 7.5 to about 8.5.

The present invention relates to immunological compositions in which the SpeAB antigen is substantially (i.e., >50%, 60%, 70%, 80%, 90%, or >99%, and values therein) adsorbed to the aluminum.

The present invention relates to immunological compositions in which the SpeAB antigen is not adsorbed (i.e., <50%, 60%, 70%, 80%, 90%, or <99%, and values therein) to the aluminum.

The present invention relates to immunological compositions in which the SpeAB antigen is at least about 80% adsorbed to the aluminum.

The present invention relates to immunological compositions in which the SpeAB antigen is less than about 20% adsorbed to the aluminum.

The present invention relates to immunological compositions comprising from about 20-100 μg/ml SpeAB; from about 0.5-1.7 mg/ml aluminum; from about 2-20% sucrose or mannitol and phosphate where the ratio of phosphate to aluminum is between from about 0.025:1 to about 1:1.

The present invention relates to immunological compositions in which also include a buffer such as, but not limited to, 10-50 mM Tris. Indeed, the compositions can include other common pharmaceutical compounds including buffers, excipients, diluents, preservatives, flavorings, and the like.

The present invention relates to methods of administering the immunological compositions and vaccines as well as methods of making these compositions.

The present invention provides a method of inducing an immunological response against *S. pyogenes* in a human subject, wherein the method comprises administering to the subject an immunological composition comprising one or more antigens derived from *S. pyogenes* such as recombinant SpeA, SpeB, and/or recombinant SpeAB antigens, and one or more of aluminum, phosphate, and/or a stabilizer.

In additional embodiments, the present invention provides a method of inducing an immunological response against *S. pyogenes* in a human subject, wherein the method comprises administering to the subject a vaccine comprising one or more antigens derived from *S. pyogenes* such as recombinant SpeA, SpeB, and/or SpeAB antigens, and one or more of aluminum, phosphate, and/or a stabilizer.

In still further embodiments, the present invention provides methods of immunizing a human subject against infection caused by *S. pyogenes*, or an illness caused by infection with *S. pyogenes* (e.g., a GAS disease), wherein the method comprises administering to the subject an immunological composition comprising one or more antigens derived from *S. pyogenes* such as recombinant SpeA, SpeB, and/or recombinant SpeAB antigens, aluminum, phosphate, and a stabilizer. Similarly, additional embodiments, provide methods of immunizing a human subject against infection caused by *S. pyogenes*, wherein the method comprises administering to the subject a vaccine comprising one or more antigens derived from *S. pyogenes* such as recombinant SpeA, SpeB, and/or SpeAB antigens, aluminum, phosphate, and a stabilizer. In various methods described herein, the present invention provides that the SpeAB antigen is present in a concentration of from about 20 to about 100 µg/ml; the aluminum is present in a concentration of from about 0.5 to about 1.7 mg/ml; the ratio of phosphate to aluminum is between about 0.025:1 to about 1:1.

In some of the method related embodiments, the immunological compositions and/or vaccines comprising a stabilizer wherein the stabilizer is sucrose and/or mannitol wherein the stabilizer is present in an amount of from about 2 to about 20% wt/wt of the immunological composition.

The present invention relates to immunological compositions and vaccines used in methods of inducing an immunological response or immunizing a subject wherein the pH of the composition is from about 7.0 to about 7.5 to about 8.5.

The present invention relates to immunological compositions and vaccines used in the various methods described herein wherein the SpeAB antigen is adsorbed to the aluminum.

The present invention relates to immunological compositions and vaccines used in the various methods described herein wherein the SpeAB antigen is not adsorbed to the aluminum.

The present invention relates to additional immunological compositions and vaccines used in the various methods described herein wherein the SpeAB antigen is at least about 80% adsorbed to the aluminum.

The present invention relates to other additional immunological compositions and vaccines used in the various methods described herein wherein the SpeAB antigen is less than about 20% adsorbed to the aluminum.

In some embodiments, the present invention provides for the use of a compound (i.e., an immunogenic composition and/or a vaccine) of the present invention for the manufacture of a medicament for treating condition such as a GAS disease, wherein the medicament is administered in a dosage regime comprising on or more administrations to a subject. In still other embodiments, the present invention provides for the use of a compound of the present invention for the manufacture of a medicament for treating a condition or disease associated with *S. pyogenes* infection or a GAS disease, wherein the medicament is prepared to be administered in a dosage regime comprising on or more administrations to a subject. Still further embodiments, provide for the use of a composition of the present invention for use in treating a GAS disease, wherein the composition (e.g., vaccine) is administered in a standard dosage or a specific dosage contemplated herein.

The present invention further provides compositions (i.e., immunological compositions and/or vaccines) arranged and/or provide in kits with without or administration instructions (e.g., a package insert) and/or one or more administration devices (e.g., tablets, pills, syringes, syrettes, transdermal administration devices, and the like). In some of these embodiments, the compositions are provided in a sufficient quantity to make a single administration to a first subject, or multiple administrations to a first subject, or one or more (e.g., several) administrations to a plurality of subjects. In still further embodiments, the package instructions are required by law, administrative rule, or medical convention by a government (e.g., the United States Food and Drug Administration ("FDA"), the United States Department of Agriculture ("USDA"), the European Medicines Agency ("EMA"), the Japanese Ministry of Health and Welfare ("MHW"), the Therapeutic Goods Administration of Australia, the State Food and Drug Administration ("SFDA") (China), the Health Protection Branch of Canada, and the Veterinary Drugs Directorate ("VDD")) or other government or professional boards.

The compositions of the present invention can be administered in one or more doses over a course of days (i.e., from 1-28, 1-30, or 1-31 days), over a course of months (i.e., from 1-12 months), to one or more (1, 2, 3, 4, 5, 6, 7, 8, 9, 10, 12, 13, 14, 15) years apart. Administrations of the compositions (e.g., immunological compositions and/or vaccines) can be administered to neonates (0-1 mo.), infants (1-12 mo.), toddlers (12-36 mo.), children (3-12 yr.), teens (13-18 yr.), adults (18 yr. and older), or the elderly (about 65 yr. and older). Accordingly, in certain embodiments, administrations of the present compositions can be given to humans from 1-52 weeks of age or at any time thereafter. Administrations of the immunological compositions and vaccines of the present invention and any other pharmaceutical of biological compositions contemplated for administration therewith can be accomplished in one or a plurality (i.e., 1 to about 10, 1 to 8, 1 to 6, 1 to 4, or 1 to 2) of times per day, or as many times (including continuous administration(s) over a set period of time) as needed to elicit the desired response in a subject.

The present invention also provides methods of administering the immunological compositions and vaccines of the present invention with one or more additional vaccines or pharmaceutical, immunological or biological compositions (e.g., antibodies, immunoglobulins, sera, therapeutic proteins, and the like) in concomitant (e.g., co-administration), sequential, or separate administrations over a period of time ranging from seconds, minutes, hours, days, to years. Suitable vaccines, pharmaceutical, immunological, or biological compositions for administration with the immunological compositions and vaccines of the present invention include, but are not limited to, commercially available products approved by a regulatory agency, such as, for example, the FDA, USDA, EMA, MHW, SFDA, or VDD. In still further embodiments, suitable vaccines, immunological, or biological compositions for administration with the immunological compositions and vaccines of the present invention include, but are not limited to, suitable anti-viral vaccines, anti-bacterial vaccines, anti-parasite vaccines, and non-infectious disease vaccines.

While the present compositions and methods of administration are not intended to be limited to any particular mechanism(s) of action, in one embodiment of the methods of the invention, the subject exhibits a higher titer of immunogen-specific antibodies, such as IgG, IgM, IgA, IgD and IgE antibodies, and/or larger numbers of immunogen-specific effector/memory T cells relative to a subject not receiving one or more administrations of the compositions. In one embodiment of the methods of the invention, the subject exhibits a higher titer or produces higher avidity serum bactericidal antibodies relative to a subject not administered the compositions.

The present invention relates to methods for formulating lyophilized (i.e., freeze dried) products. The amount of residual water or other liquid carriers, diluents, etc., in these lyophilized embodiments is between 0-2.5%, more preferably, between 0.25-1.5%, and most preferably, between 0.5-1.0% per w/w of product. While the present invention is not limited to any particular dried form or drying methodology, it is contemplated the dried products can be formed into roughly spherical beads, irregularly shaped powders or granules, cakes, sheets, or to take the form of the vessel(s) used during processing. In certain of these embodiments, the formulated product (i.e., immunological compositions, and/or vaccines) are processed (e.g., lyophilized) into roughly spherical beads of from about 500 μm to about 10 μm.

Individual antigen formulations can be formulated and subsequently processed (e.g., lyophilized), respectively, to yield bulks or stock quantities of the respective antigen/antigenic compositions and vaccines of interest (e.g., bulk SpeA, bulk SpeB, or bulk SpeAB immunogenic compositions). In some embodiments where the final product compositions are dried, for example, where the compositions are processed into powders or granules, the respective bulks can be mixed so that any desired ratio or concentration of constituent SpeA, SpeB and/or SpeAB antigens are obtained in the final composition. Mixing to obtain the desired antigen (immunogen) constituent ratios can done any time point prior to administration. In certain preferred embodiments, the compositions are formulated to the desired constituent antigen ratios prior to distribution and/or storage.

The present invention further relates to dried formulations by atomizing SpeAB in Tris and sucrose at about pH 8 in an ultralow temperature environment. In certain embodiments, the ultra-low temperature environment is provided by direct or indirect (through an intermediary) contact of the product with a liquefied gas (e.g., liquid nitrogen), or a sufficiently cooled space, wherein the product does not come into in contact with the cooling medium. Preferably, the cooling environment and/or cooling medium is sterile and/or aseptic, especially in the case where the cooling medium directly contacts the immunological compositions and/or vaccines during processing. In certain of these embodiments, the formulations are dried using conventional lyophilization and spray freeze drying ("SFD") methods, or atmospheric spray freeze drying ("ASFD") techniques.

BRIEF DESCRIPTION OF THE FIGURES

FIG. 2 shows stability of SpeAB in Tris and phosphate buffers as monitored by ELISA after 2 days of storage at 45° C.

FIG. 8A and FIG. 8B show, respectively, SpeAB antigen specific immune responses at day 14 (FIG. 8A) and day 28 (FIG. 8B).

DEFINITIONS

Figure 1A:
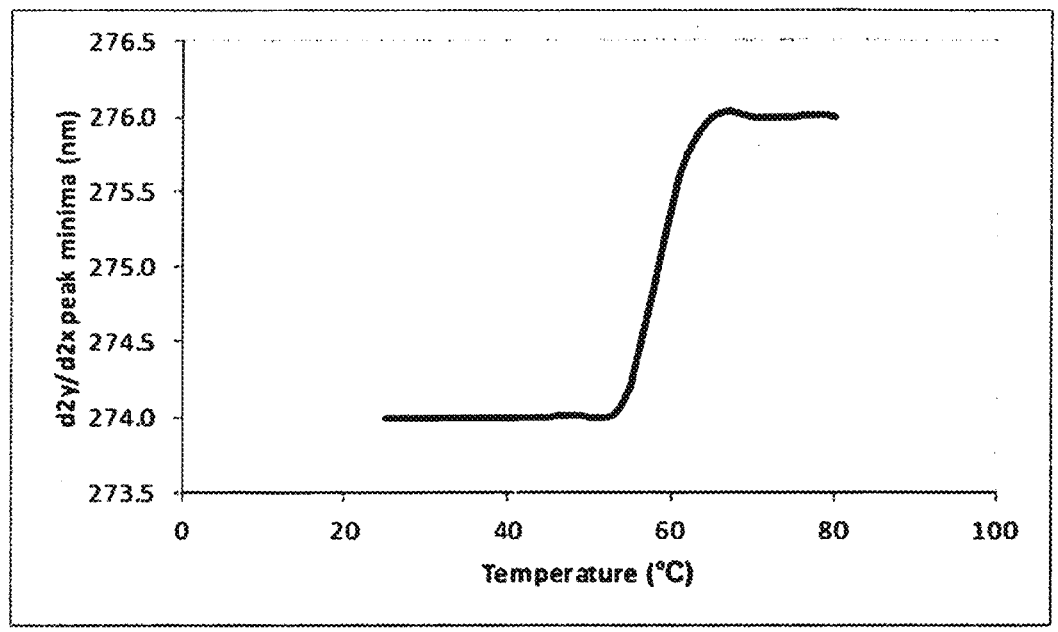
FIG. 1A shows the second derivative peak minima shift for tyrosine residues of SpeAB in phosphate buffer at pH 7.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional non-recited elements or method steps.

Throughout this application, the term "about" is used to indicate that a value includes the standard deviation of error for the device or method being employed to determine the value, or that the recited value can be slightly greater (+1, 2, or 3 units) or less (−1, 2, or 3 units) than stated.

It is contemplated that one or more members of a list provided herein may be specifically excluded from or included in a claimed invention.

As used herein, the term "immunogen" refers to an antigen that is recognized as unwanted, undesired, and/or foreign in a subject.

As used herein, the term "antigen" or "immunogenic polypeptide/peptide" is a molecule capable of being bound by an antibody or T-cell receptor. An antigen is additionally capable of inducing a humoral immune response and/or cellular immune response leading to the production of B- and/or T-lymphocytes. As used herein, the terms "superantigen," "superantigen family," or "superantigen family antigen," and grammatical equivalents, refer to an antigen/immunogen, and portions, fragments, detoxified mutants, variants and engineered recombinants thereof, selected from a group of soluble (or partially soluble) 23-29-kD staphylococci and/or streptococci proteinaceous bacterial toxins including staphylococcal enterotoxins A-E, toxic shock syndrome toxin-1 (TSST-1), and streptococcal pyrogenic exotoxins A and C that are ligands for both major histocompatibility complex (MHC) class II molecules, expressed on antigen-presenting cells, and the variable portion of the T cell antigen receptor β chain (TCR Vβ). Furthermore, in context, the *S. pyogenes* related exotoxin cysteine protease known as SpeB antigen, and recombinant SpeAB fusions, are specifically encompassed within the meaning of "superantigen" for simplicity. (Choi et al., Proc. Natl. Acad. Sci. USA, 86:8941-8945 [1989]; Fraser, J. D., Nature, 339:221-223 [1989]; Mollick et al., Science, 244:817-820 [1989]; Marrack et al., Science, 248:705-711 [1990]; and Herman et al., Annu. Rev. Immunol., 9:745-772 [1991]).

As used herein, the term "adjuvant" refers to an agent (e.g., a mineral salt) that stimulates and/or enhances an immune response in a subject. An adjuvant can stimulate and/or enhance an immune response in the absence of an immunogen (i.e., antigen) and/or can stimulate and/or enhance an immune response in the presence of an immunogen. In the present invention, a preferred adjuvant is aluminum hydroxyphosphate.

A used herein, the term "immune response" includes a response by a subject's immune system to an immunological composition or vaccine of the present invention. Immune responses include both cell-mediated immune responses (responses mediated by antigen-specific T cells and non-specific cells of the immune system) and humoral immune responses (responses mediated by antibodies present in the plasma lymph, and tissue fluids). The term "immune response" further encompasses both the initial responses to an immunogen as well as memory responses that are a result of "acquired immunity."

As used herein, the phrase "stimulating an immune response" refers to an increase in an immune response in the subject following administration of an immunological composition or vaccine composition of the present invention relative to the level of immune response in the subject absent the administration.

As used herein, the terms "immunological composition" refers to a composition that elicits an endogenous immune response in a subject (e.g., a human or other animal). The endogenous immune response may result in, for example, the switching of a Th1 biased immune response to a Th2 biased immune response, the activation or enhancement of T effector cell responses and/or the reduction of T regulatory cell response, the activation of antigen-specific naive lymphocytes that may then give rise to antibody-secreting B cells or antigen-specific effector and memory T cells or both, and/or the direct activation of antibody-secreting B cells. Similarly, as used herein, the terms "vaccine" or "vaccine composition" refer to an immunological composition as above that elicits an immune response in a subject sufficient to protect the subject from acquiring a disease for a period of time (e.g., a GAS disease).

As used herein, "prophylactic" and "preventive" fusion products, vaccines, or compositions are compositions designed and administered to prevent infection, disease, and/or any related sequelae caused by or associated with a pathogenic organism (e.g., *Streptococcus pyogenes*) in a subject such as a human.

The term "administering" includes any method of delivery of a pharmaceutical composition or agent (i.e., an immunological composition or vaccine) into a subject's system or to a particular region in or on a subject. In certain embodiments of the invention, immunological compositions and/or vaccines are administered intramuscularly, subcutaneously, intradermally, intranasally, orally, subcutaneously, transcutaneously, or transmucosally to a subject. As used herein, and as based on context, the terms "administration" or "administrations" encompass a singular or multiple instances, respectively, of the delivery of an agent to a subject such that an immunogenically effective singular delivery as well as a priming delivery (first dose or administration) and a subsequent (second, third, etc., doses or administrations) boosting delivery of an agent(s) are encompassed.

As used herein, the term "immunologically effective amount" is that amount sufficient to treat or prevent a disease and/or affect an endogenous immune response in a subject but not causing undue or unacceptable side effects or severe or excessive immune responses. The accurate dosage may vary depending on the composition(s) to be administered and the desired effect to be obtained, and may be readily determined by those skilled in the art according to factors known in medicine and vaccinology, including the patients age, weight, health, gender and sensitivity to any components or constituents of the administered composition(s) or routes and/or methods of administration. Thus, as used herein, an "immunologically effective amount" is the amount of composition sufficient to produce the desired "immunological efficacy" desired as a clinical result (e.g., disease/infection treatment and/or prevention) in a subject. An "immunologically effective amount" can be administered in one or more administrations over a set period of time, including, seconds, minutes, days, or years.

As used herein, the terms "treating" or "treatment" refer to a beneficial or desired clinical result including, but not limited to, alleviation or amelioration of one or more symptoms, diminishing the extent of infection, stabilized (i.e., not worsening) state of disease or infection, amelioration or palliation of the infectious state, and remission (whether partial or total), whether detectable or undetectable. "Treatment" can also mean prolonging survival of a subject as compared to expected survival in the absence of treatment. As used herein, "therapeutic" products, immunological composition, or vaccines, are compositions designed and administered to subjects already infected with a pathogenic organism such as *Streptococcus pyogenes*. Therapeutic vaccines (e.g., therapeutic *S. pyogenes* vaccines) are used to prevent and/or treat a GAS disease in an infected individual.

The terms "inhibiting," "reducing," or "prevention," or any variation of these terms, when used in the claims and/or the specification includes any measurable decrease or complete inhibition to achieve a desired result.

An "infection" or "infectious disease", as used herein, refers to a disorder arising from the invasion of a subject, superficially, locally, or systemically, by an infectious organism. Infectious organisms include bacteria, viruses, parasites, fungi, and protozoa. In preferred, but not limiting, embodiments of the present invention, the "infection" is caused by the bacterium *S. pyogenes*.

The term "subject," as used herein, refers to organisms to be administered the immunological compositions and/or vaccines and/or treated by the methods of the present invention. A subject includes an organism that is exposed to, suspected of being exposed to, and/or at risk of being exposed to one or more infectious agents. A subject also includes organisms to be treated so as to prevent undesired exposure to infectious agents. Furthermore, a subject includes organisms having an ineffective or inappropriate endogenous immune response to an infectious agent resulting in disease, morbidity, or subsequent sequelae. In one preferred embodiment of the invention, a subject is a human.

DESCRIPTION OF THE INVENTION

For optimal effectiveness, a vaccine should incorporate antigens from a major virulence determinant or antigens that are ubiquitously expressed by disparate bacterial strains. Streptococcal pyogenes exotoxin A (SpeA) and other secreted superantigen toxins are potential vaccinal antigen candidates for inclusion in immunological compositions and vaccines to prevent S. pyogenes infection because these proteins are virulence factors for invasive infections and are associated with many outbreaks of streptococcal toxic shock syndrome. In addition, bacteremia is commonly associated with cases of streptococcal toxic shock. The secreted polypeptide of SpeA (25,700 Mr) is classified as a superantigen that facilitates bacterial immune escape by targeting the primary recognition step in adaptive immunity. The cellular receptors for SpeA are human major histocompatibility complex (MHC) class II molecules, primarily HLA-DQ and HLA-DR proteins expressed on select cell lineages and the antigen receptors of T cells (TCRs). The normal antigen-specific signal transduction of T cells is disengaged by SpeA, displacing contacts of MHC-bound antigenic peptides with antigen combining site elements of the TCR, and results in an elevated polyclonal activation of T cells. Toxic shock may ensue from pathological levels of tumor necrosis factor alpha (TNF-α) and other proinflammatory cytokines released in response to secreted superantigens.

Most S. pyogenes M protein serotypes express an extracellular cysteine protease (streptopain) historically termed streptococcal pyrogenic exotoxin B (SpeB) though not homologous in structure or function to SpeA or any other superantigen. Co-purification of contaminant streptococcal proteins with SpeB led to the erroneous conclusion that the protease was a superantigen. The secreted protease SpeB is also a bacterial surface molecule with binding activity to laminin and other glycoproteins making it a potential target to opsonizing antibodies. The protease is an important colonization and pathogenicity factor reported to modify several host substrates. For example, the purified SpeB cleaves interleukin 1 precursor protein to produce active interleukin 1 and also cleaves extracellular matrix proteins fibronectin and vitronectin thus modulating entry of S. pyogenes into host cells. Although multiple alleles exist, polyclonal antisera generated against one SpeB allelic product reacts with SpeB from all S. pyogenes M1 serotypes examined in patients with invasive S. pyogenes infections of either streptococcal toxic shock syndrome and/or necrotizing fasciitis. The ubiquitous expression of SpeB by S. pyogenes strains and the conserved nature of the antigenic determinants recognized by antibodies are noteworthy features, thus fulfilling major criteria for a potential vaccine.

A recombinant protein fusion between Streptococcal pyrogenic exotoxin B (SpeB) and Streptococcal pyrogenic protein A (SpeA) is needed in the art. The SpeAB fusion protein is preferably composed in part of a genetically attenuated superantigen toxin protein. This purified protein has been modified so that the superantigen attributes are absent but the superantigen is effectively recognized by the immune system and an appropriate antibody response is produced. A mutant, catalytically inactive SpeB is used as a fusion partner to SpeA. Based on analysis of the catalytic site structure from crystallographic data mutation of active site residues is sufficient to inactivate proteolytic activity. Potency studies in mice demonstrated the potential for the SpeAB fusion to protect against both toxic shock and bacterial infection.

The present invention relates to immunological compositions and vaccines which target diseases caused by infection with Streptococcus pyogenes. The immunological compositions and vaccines of the present invention in part utilize a recombinant fusion protein (SpeAB) which comprises SpeA, a secreted toxin, and SpeB, a surface bound and secreted cysteine protease. (See, Ulrich, R., J. Immun. Based Therapies and Vaccines, 6(1):8 [2008]). A combination of the SpeA and SpeB virulence factors in a recombinant SpeAB fusion has been found to provide protection against most strains of the Streptococcus pyogenes.

The present invention relates to stabilized and more highly immunogenic formulations of the SpeAB vaccine that are safe and potent by providing robust vaccine formulations that address the formerly limiting biophysical characteristics of the SpeAB fusion as well environmental factors such as pH, ionic strength, and temperature impact the antigen. Various embodiments of the present invention provide formulations in which interactions of one or more aluminum adjuvants with the other constituents of the immunogenic compositions and/or vaccines of the present invention form optimized systems controlled to provide final formulations where the antigen(s) of interest (e.g., SpeAB) are either adsorbed, non-adsorbed, or partially adsorbed to an adjuvant (e.g., aluminum) as required.

The immunogenic compositions provided by the present invention for use according to the methods described herein and as known in the immunization art may be delivered as a standard injectable dose (e.g., about 0.5 ml) and contain from about 0.1 µg to about 500 µg, or from about 0.1 µg to about 200 µg, or from about 0.1 µg to about 100 µg, or from about 0.1 µg to about 50 µg, or from about 0.1 µg to about 35 µg, or from about 0.1 µg to about 25 µg, or from about 0.1 µg to about 20 µg, or from about 0.1 µg to about 15 µg, or from about 0.1 µg to about 10 µg, or from about 0.1 µg to about 5 µg, or from about 1 µg to about 100 µg, or from about 1 µg to about 50 µg, or from about 1 µg to about 35 µg, or from about 1 µg to about 25 µg, or from about 1 µg to about 20 µg, or from about 1 µg to about 15 µg, or from about 1 µg to about 10 µg, or from about 1 µg to about 5 µg, or from about 5 µg to about 100 µg, or from about 5 µg to about 50 µg, or from about 5 µg to about 35 µg, or from about 5 µg to about 25 µg, or from about 5 µg to about 20 µg, or from about 5 µg to about 15 µg, or from about 5 µg to about 10 µg of antigen (and values therein).

The interaction of SpeAB with aluminum hydroxide adjuvants indicate that the antigen binds more tightly with the adjuvant surface over time. Tight binding to the adjuvant surface has the potential to adversely effect the potency of SpeAB through interference of antigen processing and presentation by antigen presenting cells. To avoid potential impacts on antigen potency it was desirable to understand the interactions of SpeAB with aluminum adjuvants. Formulation conditions were developed whereby the majority of the antigen was either weakly adsorbed to the adjuvant surface or where most of the antigen not adsorbed. This may be achieved by utilizing a series of charged aluminum surfaces ranging from positively charged aluminum hydroxide adjuvant to negatively charged aluminum phosphate adjuvant. Aluminum hydroxide adjuvant can be treated with increasing amounts of phosphate ion to decrease the surface charge of the adjuvant. Phosphate in solution can exchange with surface hydroxyls of aluminum hydroxide adjuvant due to higher affinity for aluminum.

At pH 8.0, untreated aluminum hydroxide adjuvant has a positive surface charge and as the level of phosphate increases the surface charge of the adjuvant decreases and becomes negative. The calculated isoelectric point (pI) of SpeAB is 6.4 however, the components of the fusion protein SpeA and SpeB have pI's of 5.6 and 8.6 respectively. This suggests that at pH 8 the two sections of the protein may have opposite charges resulting in directional adsorption depending on the surface charge of the adjuvant. This is supported by adsorption data obtained in Tris buffer as the majority of the SpeAB is not desorbed until the adjuvant was treated with a 1:1 ratio of phosphate to aluminum. Based on a pI of 6.4 for SpeAB it would be anticipated that the majority of the antigen would be desorbed at a much lower concentration of phosphate.

Moreover, the presence of a stabilizer, such as sucrose influences the extent to which the antigen is adsorbed. Adsorption of SpeAB in the presence of sucrose stabilizer at 0.025 and 1 molar ratio phosphate treated aluminum hydroxide has a significant impact on the non-adsorbed formulation. The 1:1 molar ratio of phosphate to aluminum provided a formulation in which the antigen is 69% adsorbed. The adsorbed formulation (0.025:1 molar ratio of phosphate treatment) had a value of 87% SpeAB adsorbed.

Formulations in which the phosphate to aluminum treatment ratios of about 1.5:1 and 2:1 were analyzed and the results indicate that a 2:1 ratio of phosphate treated aluminum hydroxide adjuvant is necessary to achieve <20% adsorption of the SpeAB antigen in the presence of 10% sucrose.

As described herein, in certain embodiments, suitable stabilizers including, but are not limited to, sucrose and mannitol. One or more stabilizers can be added to the formulations of the present invention. The stabilizers may be present at a level of about 30% or less, or about 25% or less, or about 20% or less, or about 15% or less, or about 10% or less, or about 5% or less. Additionally, the stabilizers may be present at a level of about 1% to about 30%, or about 1% to about 25%, or about 1% to about 20%, or about 1% to about 15%, or about 1% to about 10%, or about 1% to about 5%, or about 5% to about 30%, or about 5% to about 25%, or about 5% to about 20%, or about 5% to about 15%, or about 5% to about 10% (and values therein) of the total composition.

The present invention also relates to methods and formulations wherein the pH of the formulation is suitable to keep the SpeAB antigen stable. In some embodiments, the pH of the solution may be 8.0 or lower, or about 7.5 or lower, or about 7.0 or lower. In other embodiments, the pH of the solution may be between about 6.0 to about 8.0, or about 6.5 to about 8.0, or about 7.0 to about 8.0, or about 7.5 to about 8.0. The pH of the immunological compositions and/or vaccines of the present invention can be modified with the suitable buffers. Standard techniques for buffering the pH of solutions are understood in the art.

The present invention provides novel compositions and formulations as well as methods of making these compositions and formulations that are more stable than existing antigenic formulations made by conventional. For example, in preferred embodiments, the present invention provides immunogenic SpeAB formulations that are at least 10% more, or are at least 20% more, or are at least 30% more, or are at least 40% more, or are at least 50% more, or are at least 60% more, or are at least 70% more, or are at least 80% more, or are at least 90% more, or are at least 100% more stable than solutions with similar components. In particular embodiments, the oral suspension formulations of the present invention are about 5% to 500% more stable, or about 5% to about 100%, or about 5% to about 90%, or about 5% to about 80%, or about 5% to about 70%, or about 5% to about 60%, or about 5% to about 50%, or about 5% to about 40%, or about 5% to about 30%, or about 5% to about 20%, or about 5% to about 10%, or about 10% to about 500%, or about 10% to about 100%, or about 10% to about 90%, or about 10% to about 80%, or about 10% to about 70%, or about 10% to about 60%, or about 10% to about 50%, or about 10% to about 40%, or about 10% to about 30%, or about 10% to about 20%, or about 25% to about 500%, or about 25% to about 100%, or about 25% to about 90%, or about 25% to about 80%, or about 25% to about 70%, or about 25% to about 60%, or about 25% to about 50%, or about 25% to about 40%, or about 50% to about 500%, or about 50% to about 100%, or about 50% to about 90%, or about 50% to about 80%, or about 50% to about 70%, or about 50% to about 60%, or about 75% to about 500%, or about 75% to about 250%, or about 75% to about 100% (and values therein) more stable than solutions with similar components (constituents).

The compositions of the present invention may be produced using various formulation technologies that include spray freeze drying processes to effectively coat the vaccine compositions. Spray freeze drying is known to enable the production of powder particles with well-defined physical properties including low density, high surface area, well defined particle size distribution and potentially very rapid dissolution. The present invention relates to vaccine particles coated with an ASFD process which can confer desirable particle physical properties, though with reduced risk of thermal and pressure differential damage to sensitive, antigenic structure. Atmospheric spray freeze drying also has the advantage of lending itself to large scale continuous processing.

During ASFD a carefully formulated liquid solution is atomized to a specifically sized spherical droplet and immediately frozen, locking in the size and shape of each individual particle. The particles are then dried by passing a cryogenic gas (e.g., nitrogen) through the particle bed. The flow and temperature profiles can be customized to give the particles the desired morphology for their eventual application. Because of the use of convective heat transfer, the process is usually much quicker than lyophilization and the elimination of the need for high vacuum lowers cost and facilitates transition to a manufacturing scale. Thus far there are only a few examples in the literature where lyophilization, spray drying, and spray freeze drying protocols have been employed to prepare controlled-release solid-dosage products intended for oral delivery of therapeutics, and in a fewer cases, of actual vaccines products. Spray drying has been successful in preparing well defined particles, but this technology requires the application of heat which may affect the potency of immunogenic proteins by causing denaturation. Lyophilization and spray freeze drying methodologies employ cryoprotectants to stabilize the 3D structure of proteins during the drying process. However, lyophilization forms particles with irregular shape and have non-homogeneous drug-to-polymer distributions, which can cause undesirable release profiles. Spray freeze drying methods are useful in producing protein-based dry particles, but in preferred embodiments, the ASFD method is preferred, as it does not expose sensitive proteins to the stresses of major differential pressures during processing which can degrade the proteins. In certain embodiments, there are a variety of possible cryoprotectants that can be used including, but not limited to, mannitol, lactose, sorbitol, and sucrose, and combinations thereof. Atmospheric spray freeze drying utilizes atomizing nozzles which are used to produce ideal particle physical properties such as uniform coacervation of the formulation.

Pharmaceutical Forms, Formulations, and Additional Constituents

The compositions of the present invention can be administered alone or as admixtures with preferred conventional excipients, for example, pharmaceutically, or physiologically, acceptable organic, or inorganic carrier substances suitable for enteral or parenteral application which do not deleteriously react with the composition. In certain embodiments, preferred suitable pharmaceutically acceptable carriers include water, salt solutions (such as Ringer's solution), alcohols, oils, gelatins and carbohydrates such as lactose, amylose or starch, fatty acid esters, hydroxymethylcellulose, and polyvinyl pyrolidine. Such preparations can be sterilized (e.g., sterile filtered) and, if desired, mixed with auxiliary agents such as lubricants, preservatives, stabilizers, wetting agents, emulsifiers, salts for influencing osmotic pressure, buffers, coloring and/or aromatic substances and the like which do not deleteriously react with the compositions administered to the human. Preferred diluents for diluting the vaccines of the present invention include but are not limited to 150 mM NaCl with histidine and trehalose. Additional embodiments embodying the immunogenic compositions and vaccines as well as methods of formulating and administering these compositions within the scope of the present invention are provided below. In particular, alternative pharmaceutical forms, formulations, composition constituents (i.e., elements), dosages, administration regimes, and the like are described herein. All constituents of the compositions whether biologically, or more particularly immunologically active (i.e., immunogens, antigens, adjuvants, and the like) or conversely inert (e.g., excipients, diluents, buffers, and the like) are selected such that they do not deleteriously react (e.g., acutely diminish stability or immunological efficacy and the like) with other constituents of the composition or produce untoward or adverse reactions in a subject. Depending on the condition being treated, preferred embodiments of the present invention are formulated and administered systemically or locally.

The immunogenic compositions and vaccines of the present invention may also include a pharmaceutically acceptable carrier. As used herein, a "pharmaceutically acceptable carrier" refers to any substance or vehicle suitable for the intended route of administration of the compositions comprising at least one antigen and/or immunogen (e.g., SpeA, SpeB, and/or SpeAB, and/or other superantigens). A pharmaceutically acceptable carrier includes any and all excipients, solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired and that are physiologically compatible (see, e.g., Remington's The Science and Practice of Pharmacy, 21st Ed., A. R. Gennaro, Lippincott, Williams & Wilkins, Baltimore, Md., [2006]; the entire contents of which are incorporated herein by reference). Additionally, exemplary pharmaceutical formulation methods and methods of producing pharmaceuticals useful in certain embodiments are described in U.S. 20030211046A1; U.S. 20030004182A1; U.S. 2002060356384; U.S. 20020015728A1; U.S. Pat. No. 6,511,660; U.S. Pat. No. 6,406,745; U.S. Pat. No. 6,346,269; U.S. Pat. No. 6,039,977; U.S. Pat. No. 5,858,408; U.S. Pat. No. 5,631,023; U.S. Pat. Nos. 5,476,667; 5,044,091; U.S. Pat. No. 4,867,970; and WO 0028969A2 (each of which is incorporated herein by reference in its entirety).

Suitable pharmaceutically acceptable excipients used in the compositions of the present invention include, but are not limited to, inert diluents, dispersing and/or granulating agents, surface active agents and/or emulsifiers, disintegrating agents, binding agents, preservatives, buffering agents, lubricating agents, and/or oils.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (e.g., starch 1500), microcrystalline starch, water insoluble starch, calcium carboxymethyl cellulose, magnesium aluminum silicate, sodium lauryl sulfate, quaternary ammonium compounds, and combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate, polyoxyethylene sorbitan, polyoxyethylene sorbitan monooleate, sorbitan monopalmitate, sorbitan monostearate, sorbitan tristearate, glyceryl monooleate, sorbitan monooleate), polyoxyethylene esters (e.g., polyoxyethylene monostearate, polyoxyethylene hydrogenated castor oil, polyethoxylated castor oil, polyoxymethylene stearate), sucrose fatty acid esters, polyethylene glycol fatty acid esters, polyoxyethylene ethers, (e.g., polyoxyethylene lauryl ether), poly(vinyl-pyrrolidone), diethylene glycol monolaurate, triethanolamine oleate, sodium oleate, potassium oleate, ethyl oleate, oleic acid, ethyl laurate, sodium lauryl sulfate, block copolymers based on ethylene oxide and propylene oxide, nonionic triblock copolymers of polyoxypropylene), cetrimonium bromide, cetylpyridinium chloride, benzalkonium chloride, docusate sodium, and/or combinations thereof.

Exemplary binding agents include, but are not limited to, pharmaceutical grades of starches (e.g., cornstarch and starch paste), gelatin, sugars/sugar alcohols (e.g., sucrose, glucose, dextrose, dextrin, molasses, lactose, lactitol, mannitol), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, and polyvinylpyrrolidone), aluminum silicate, magnesium, magnesium stearate, magnesium carbonate, alginates, polyethylene oxide, polyethylene glycol, inorganic calcium salts, sodium saccharin, talcum, silicic acid, polymethacrylates, waxes, water, alcohol and the like, and combinations thereof.

Exemplary preservatives include, but are not limited to, antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, and potassium metabisulfite. In certain embodiments, the preservative is an antioxidant. In certain other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, and ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

Exemplary oils include, but are not limited to, almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Typically, vaccines are administered in a manner compatible with a vaccine formulation, and in such amount as will be therapeutically effective and/or immunogenic. The quantity to be administered depends on the subject to be treated, including the capacity of the individual's immune system to synthesize antibodies and the degree of protection desired. Precise amounts of active ingredient required to be administered depend on the judgment of the practitioner or health regulator. Typically, from about 0.1, to 1, to 5, to 10, to 20, to 30, to 40, to 50, to 60, to 70, to 80, to 90, to 100 ng, µg, or mg may be administered per vaccination or administration.

Suitable regimes for initial administration and booster shots are also variable, but are typified by an initial administration followed by subsequent inoculations or other administrations. In some embodiments, from 1, 2, 3, 4, 5, . . . 10, . . . 20, . . . 35, . . . 55, . . . 100, . . . 1,000, . . . 10,000 or more units of time (e.g., minutes, hours, days, weeks, etc.) pass between the first administration of a composition and subsequent administration(s) to the subject. In some of these embodiments, the interval(s) between any two or more administrations are constant (e.g., of equal duration). In still other embodiments, the interval(s) between any two or more administrations are varied (e.g., not of equal duration). Varied intervals can be either random or repeating and formulaic. Those skilled in the art will appreciate the steps necessary for designing and adjusting the dosing schedules and/or the dosing order of compositions or therapies as mentioned herein.

Methods and schemes for administering and sufficiently dosing immunological compositions, vaccines, and adjuvant systems are known within the art and are described herein. Other therapeutic regimens or agents can be used in conjunction with the methods and compositions of the present invention.

Exemplary routes of administration to the subject can be through the eyes (opthalmic), mouth (oral), skin (transdermal), nose (nasal), lungs (inhalant), oral mucosa (buccal), ear, etc., by injection (e.g., intravenously, subcutaneously, intratumorally, intraperitoneally, etc.) and the like. In specific embodiments, suitable routes of administration include, for example, oral or transmucosal administration as well as parenteral delivery (e.g., intramuscular, subcutaneous, intramedullary, intrathecal, intraventricular, intravenous, intraperitoneal, or intranasal administration). A brief review of methods for drug delivery is provided by Langer, Science, 249:1527-1533 (1990).

Certain injectable preparations for example, sterile injectable aqueous or oleaginous suspensions, A sterile injectable preparation may be a sterile injectable solution, suspension or emulsion in a nontoxic parenterally acceptable diluent or solvent, for example, as a solution in 1,3-butanediol, using physiological saline, aqueous solutions such as Ringers solution, U.S.P., isotonic sodium chloride solution, and non-aqueous solutions, such as vegetable oils, high fatty acid esters (e.g., ethyl oleic acid, etc.), alcohols (e.g., ethanol, benzylalcohol, propylene glycol and glycerin, etc.). The injectable preparation(s) may be supplemented with pharmaceutical carriers, which are exemplified by a stabilizer for preventing degeneration (e.g., ascorbic acid, sodium hydrogen sulfite, sodium pyrosulfite, BHA, tocopherol, EDTA, etc.), or reagents, and techniques, for facilitating solidification/semi-solidification of the preparation(s) (e.g., foam drying, freeze-foam drying, spray drying (atomization), spray-freeze-drying, evaporative drying, percolative drying, vacuum drying, lyophilization, micropelleting, prilling, and variations thereof, etc.), an emulsifier(s), an excipient(s), a buffering agent for pH adjustment, and a preservative for inhibiting contamination, including but not limited to, microbial growth (e.g., phenylmercury nitrate, thimerosal, benzalkonium chloride, phenol, cresol, benzylalcohol, etc.), and other appropriate reagents Generally Regarded as Safe (i.e., GRAS reagents). Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In addition to standard needle delivered formulations and methods of administration (e.g., intramuscular and transcutaneous and the like), certain formulations and embodiments of the compositions and methods of the present invention are suitable for delivery using intradermal delivery devices (i.e., short singular or plural needle arrays) such as those described in U.S. Pat. Nos. 4,886,499; 5,190,521; 5,328,483; 5,527,288; 4,270,537; 5,015,235; 5,141,496; and 5,417,662. Accordingly, compositions formulated for intradermal delivery may be administered by devices that limit the effective penetration of a needle into the skin, such as those described in PCT publication WO99/34850 and functional equivalents thereof. In still further embodiments, jet injection devices which deliver liquid vaccines to the dermis via a liquid jet injector and/or via a needle which pierces the stratum coraeum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537 (each of which is incorporated by reference in its entirety). In yet other embodiments, ballistic powder/particle delivery devices that use compressed gas to accelerate a vaccine in powder form through the outer layers of the skin to the dermis are suitable. Alternatively, or additionally, conventional syringes may be used in the classical mantoux method of intradermal administration.

Compositions for oral administration are typically liquid or in solid dosage forms. Compositions for oral administration may include protease inhibitors, including organic acids such as citric acid, in order to inhibit pancreatic and brush border proteases. Compositions for oral administration may additionally include absorption enhancers, such as acylcarnitine and lauroylcarnitine, to facilitate the uptake of the peptide through the lumen of the intestine into the systemic circulation by a paracellular transport mechanism. Compositions for oral administration may additionally include detergents to improve the solubility of the peptides and excipients and to decrease interactions with intestinal mucus. Solid form compositions for oral administration, such as tablets or capsules, may typically comprise an enteric coating which further protects the peptides from stomach proteases and permits passage of the tablet or capsule into the small intestine. The solid form composition may additionally comprise a subcoat such as a non-ionic polymer. Examples of preparation of such orally available formulations are disclosed in U.S. Pat. No. 5,912,014; U.S. Pat. No. 6,086,918; and U.S. Pat. No. 6,673,574. The disclosure of each of these documents is hereby incorporated herein by reference.

In particular solid formulation embodiments intended for oral administration, the compositions are presented as capsules, tablets, pills, powders, or granules. In certain of these solid dosage forms, the active ingredients (e.g., SpeA, SpeB, and/or SpeAB and/or adjuvant(s)) are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the composition may comprise buffering agents.

Solid compositions of a similar type may be employed as fillers in soft- and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft- and hard-filled gelatin capsules using such excipients as lactose or milk sugar as well as high molecular weight polethylene glycols and the like.

The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

In certain embodiments, exemplary techniques and reagents for solidification/semi-solidification of the compositions in particular embodiments may be found in, for example, U.S. Pat. No. 5,307,640; U.S. Pat. No. 5,897,852; U.S. Pat. No. 6,106,836; U.S. Pat. No. 6,458,363; U.S. Pat. No. 7,836,606; U.S. Ser. No. 12/397,140; U.S. Ser. No. 12/500,156; and EP 0 689 867B1; EP 0 799 613B1; EP 1 140 152B1; EP 1 794 524B1; WO 2003/072016; WO 2004/073652; WO 2006/008006; FR 1054443; and FR 1056961, each of which is incorporated herein by reference in its entirety.

In still other embodiments, for aerosol administration, the compositions and vaccines of the present invention are preferably supplied in finely divided form along with a surfactant and propellant. The surfactant must, of course, be nontoxic, and preferably soluble in the propellant. Representatives of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, such as the inclusion of lecithin for intranasal delivery.

Formulations suitable for nasal administration may, for example, comprise from about as little as 0.1% (w/w) and as much as 100% (w/w) of the active ingredient, and may comprise one or more of the additional ingredients described herein. A vaccine of the invention may be prepared, packaged, and/or sold in a formulation suitable for buccal administration. Such formulations may, for example, be in the form of tablets and/or lozenges made using conventional methods, and may, for example, comprise about 0.1% to 20% (w/w) active ingredient, the balance comprising an orally dissolvable and/or degradable composition and, optionally, one or more of the additional ingredients. Alternately, formulations suitable for administration to buccal mucosa may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 μm to about 200 μm, and may further comprise one or more of the additional ingredients (constituents).

EXAMPLE

Example 1 pH Stability Study Using Derivative Spectroscopy

A pH stability profile was determined using derivative spectroscopy as well as SDS-PAGE to monitor physical stability, and ELISA to monitor immunological epitope stability of the SpeAB antigen. Solutions containing 100 μg/ml SpeAB were prepared at pH 7, 7.5, and 8 in phosphate buffer and 8, 8.5, and 9 in Tris buffer. Spectra of each sample were taken while increasing the temperature from 25°-80° C. The melting temperature ($T_m$) of SpeAB (Table 1) was calculated by first determining the second derivative of the spectra with a triangular smooth.

TABLE 1

Melting temperatures for SpeAB antigen at various pHs in phosphate or tris buffer

| Buffer | pH | Tm (° C.) |
| --- | --- | --- |
| phosphate | 7 | 58 |
| | 7.5 | 62 |
| | 8 | 60 |
| Tris | 8 | 62 |
| | 8.5 | 55 |
| | 9 | 60 |

Figure 1B:
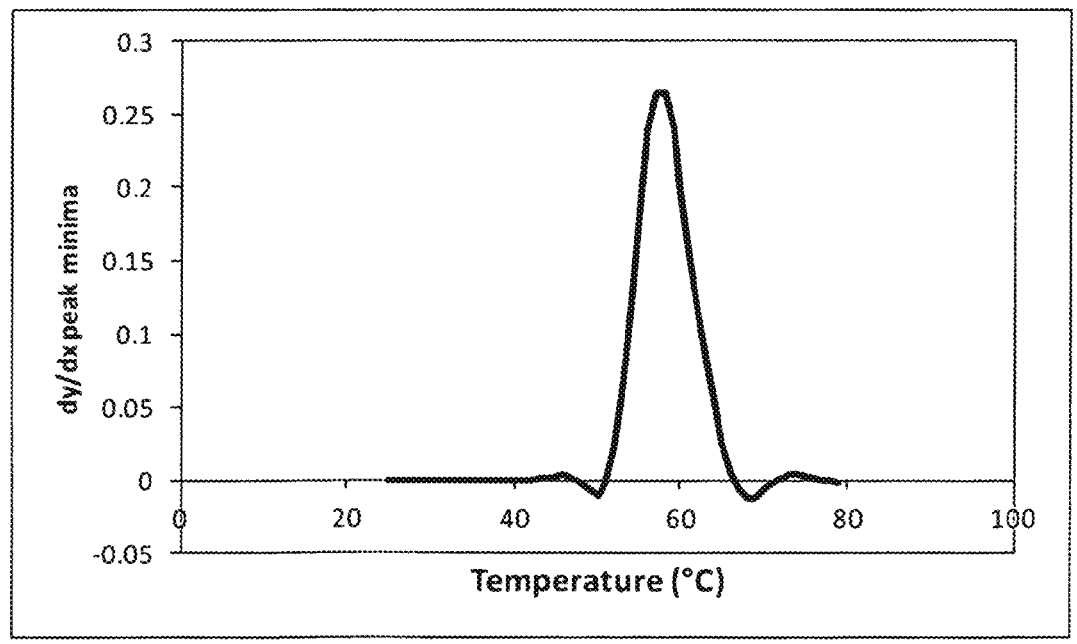
FIG. 1B shows the melting temperature of SpeAB determined as the inflection point of the peak minima curve. The melting temperature was calculated as the peak from the derivative of the original curve.
Figure 3A:
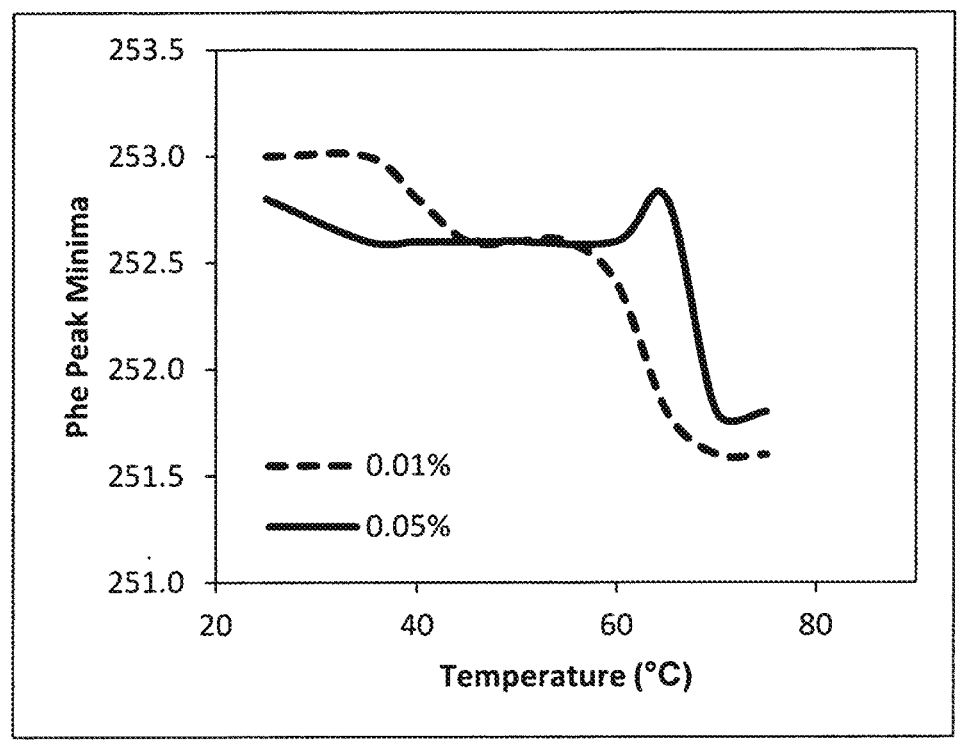
FIG. 3A and FIG. 3B show, respectively, the second derivative peak minima shift for phenylalanine residues of SpeAB in Tris buffer at pH 8 with added Tween 20 (FIG. 3A); and, the melting temperature of SpeAB determined as the inflection point of the peak minima curve calculated as the peak minima from the derivative of the original curve observing there was a shift was to a blue wavelength (FIG. 3B).
Figure 3B:
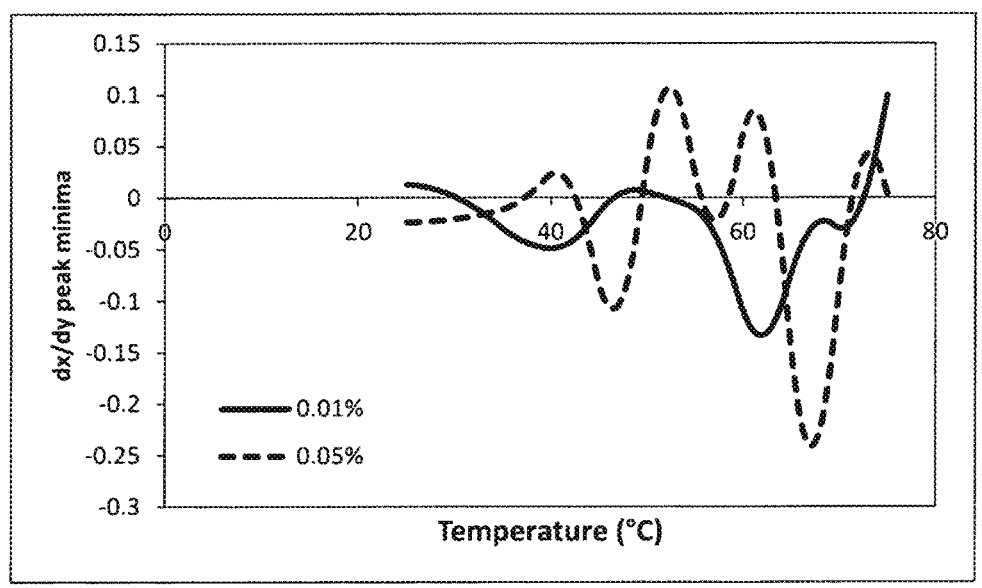
Figure 4:
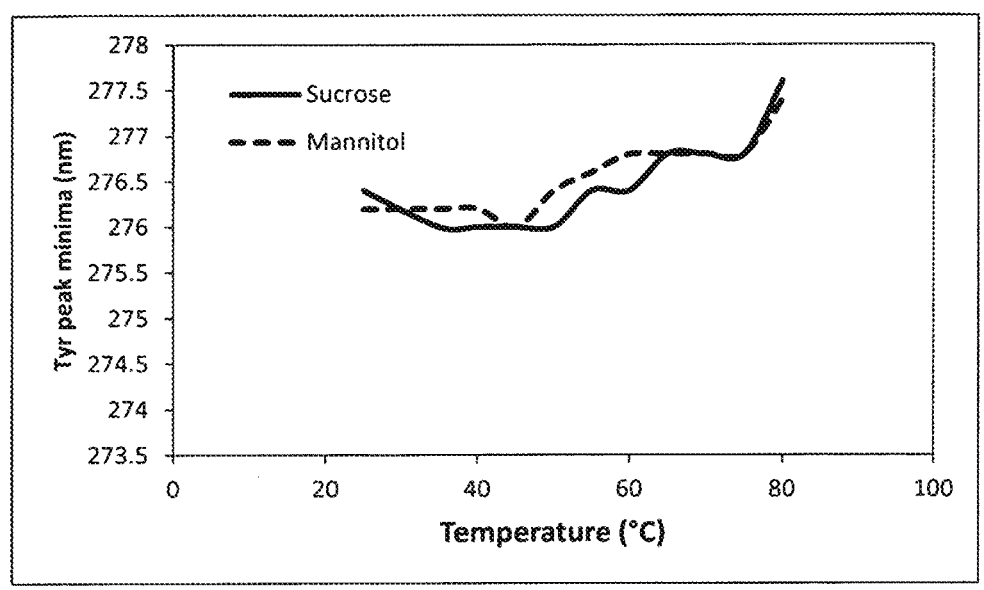
FIG. 4 shows the second derivative peak minima shift for tyrosine residues of SpeAB in Tris buffer at pH 8 with added sucrose and mannitol.

The peak shift attributed to tyrosine was used to monitor stability. (FIG. 1A). The red shift in the tyrosine peak minima indicates that there is an aggregation process occurring in the samples. The $T_m$ was determined by calculating the inflection point of the curve by the first derivative. This analysis was repeated for SpeAB in phosphate buffer at pH 7.5 and 8 as well as Tris buffer at pH 8, 8.5, and 9. The derivative spectroscopy data suggest that SpeAB has optimum stability at pH 7.5 in phosphate buffer and pH 8 in tris buffer. SpeAB pH/stability was also monitored by SDS-PAGE. The data demonstrated that at pH 8 and below there was no significant degradation of the antigen. Above pH 8 a decrease of intact antigen can be observed over the four days of storage at 45° C. (FIG. 1B).

pH Stability Study Using ELISA Assays

SpeAB analysis by ELISA was performed in which samples were diluted 25 fold in coating buffer (20 mM tris, 150 mM NaCl, pH 9) and 100 μl was placed in duplicate in the appropriate well of a 96 well plate. Standard were prepared by performing six, 2-fold serial dilutions starting at 4 μg/ml in the appropriate wells of the plate. The plate was incubated for 1 hour at 37° C. and then washed 3 times with 100 μl/well of washing buffer (20 mM $PO_4$, 150 mM NaCl, pH 7.4). Next, 100 μl/well of blocking buffer (100 μg/ml BSA, 20 mM $PO_4$, 150 mM NaCl, pH 7.4) was added to the plate and the plate was incubated for 1 hour at 37° C. The plate was washed as before and 100 μl/well of a 1:25,000 dilution of rat anti-SpeAB antisera was added to the plate and the plate was incubated for 1 hour at 37° C. The plate was washed as before and 100 μl/well of a 1:70,000 dilution of goat anti-rat IgG-HRP was added to the plate and the plate was incubated for 1 hour at 37° C. The plate was washed as before and 100 μl/well of TMB reagent was added to the plate and the plate was incubated for 20 minutes at room temperature. The reaction was stopped by addition of 100 μl/well 3 M $H_2SO_4$ and the absorbance of the wells was monitored at 450 nm. The concentration of SpeAB in each sample was determined by calculation from the standard curve (FIG. 2).

Example 2

Additive Stability Studies

One of the primary degradation mechanisms for the SpeAB antigen is unfolding followed by aggregation. An excipient stabilizer, Tween 20, a non-ionic surfactant, was added at 0.01% and 0.05% to the SpeAB at pH 8 and the physical stability was monitored by derivative spectroscopy. For this analysis, the phenylalanine peak was used and the melting temperature for the 0.01% added Tween 20 was 62° C. and for 0.05% added tween was 67° C. This indicates that the higher level of Tween 20 was able to stabilize the unfolding of SpeAB.

Figure 5:
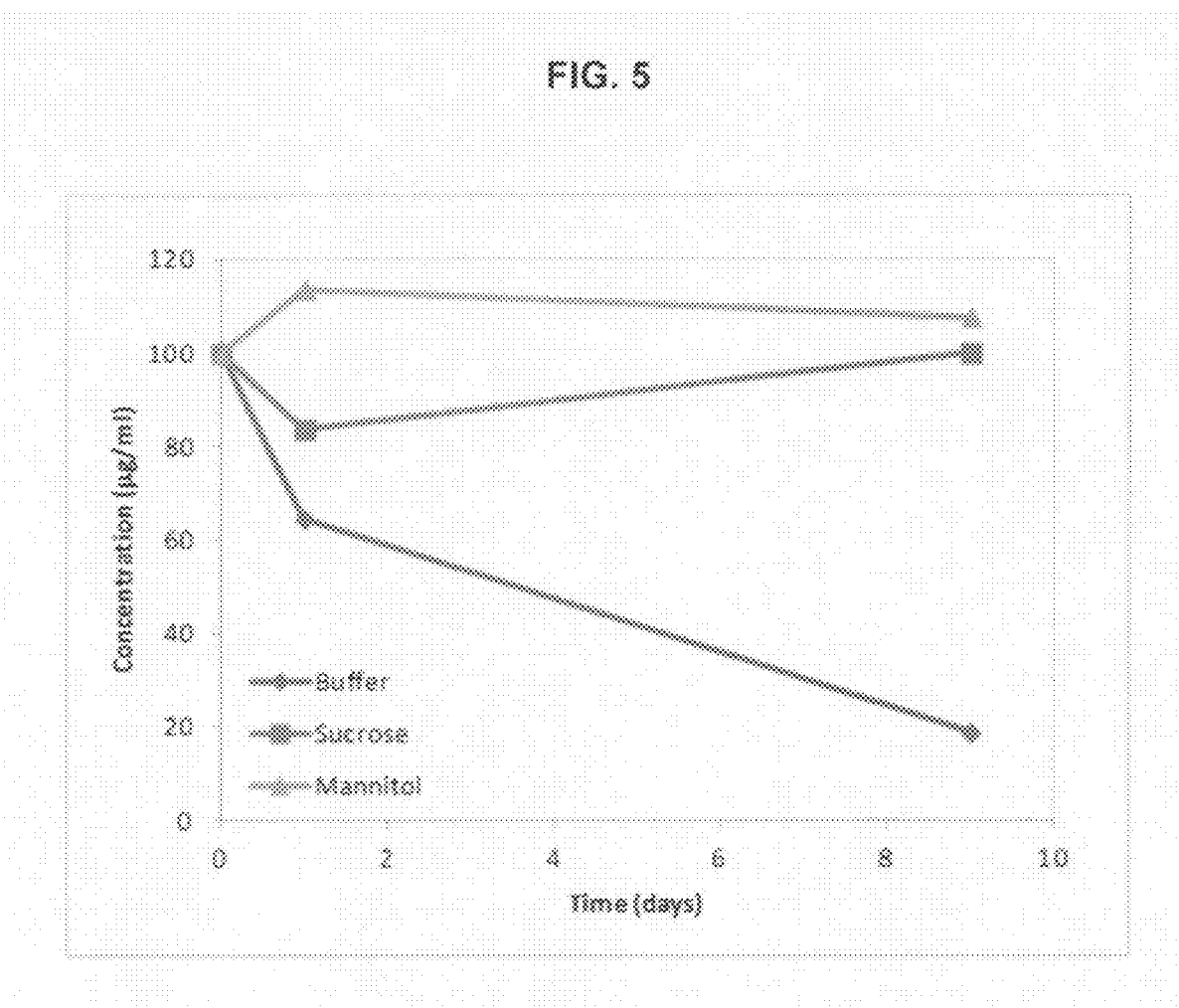
FIG. 5 shows stability of SpeAB with added 10% sucrose or mannitol as monitored by ELISA following storage at 45° C. for 9 days.
Figure 6:
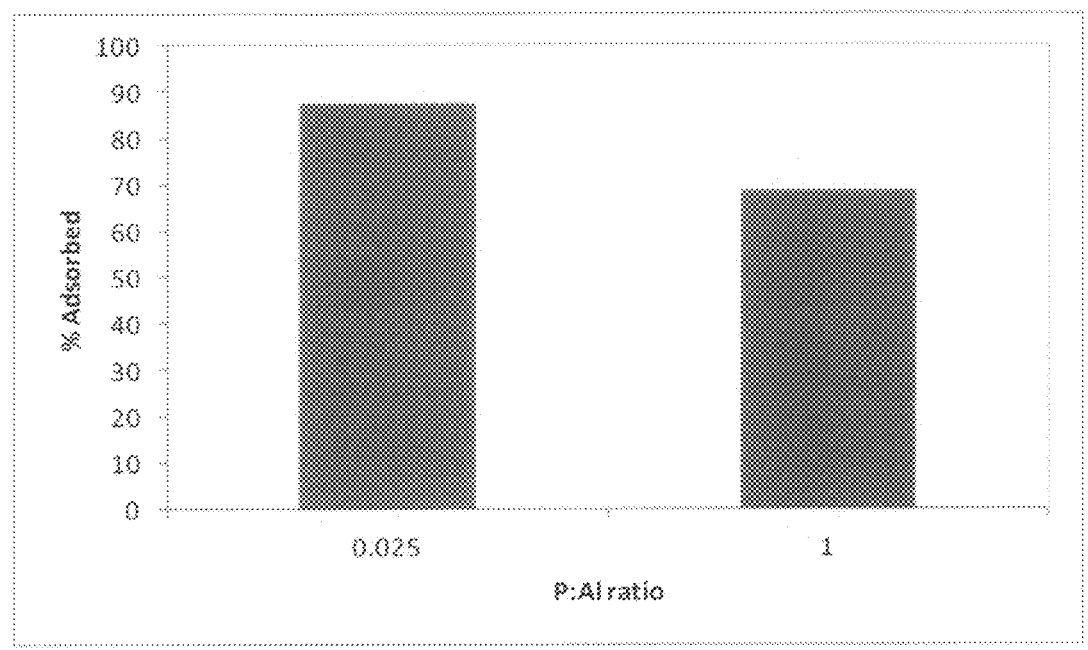
FIG. 6 shows adsorption of SpeAB on phosphate treated aluminum hydroxide adjuvant with 10% sucrose stabilizer.
Figure 7:
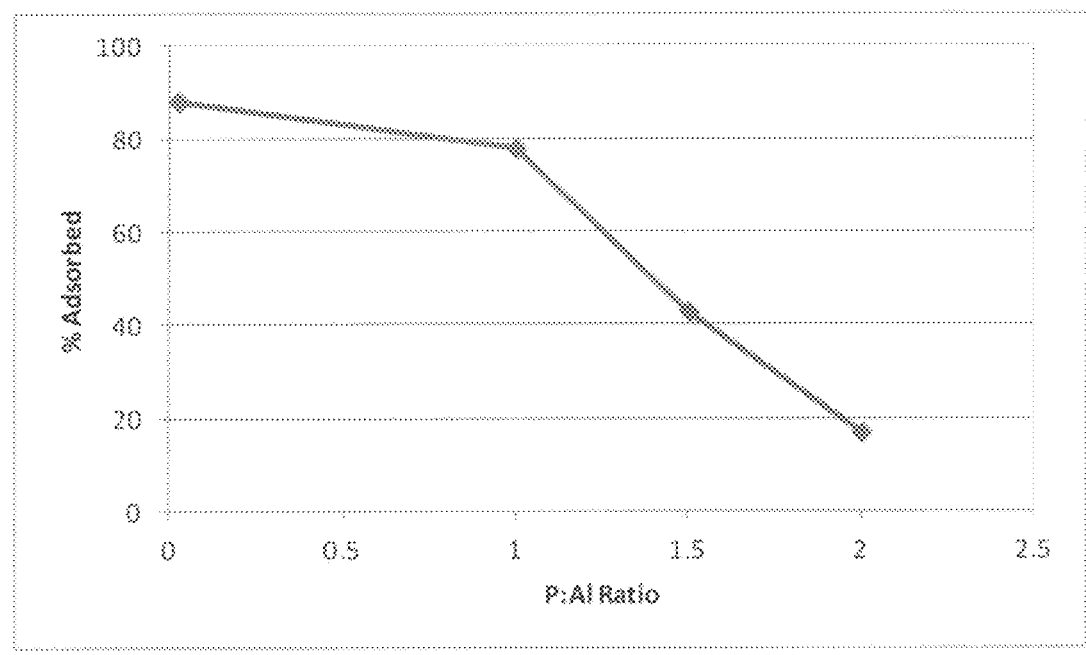
FIG. 7 shows adsorption of SpeAB on phosphate treated aluminum hydroxide adjuvant with 10% sucrose stabilizer.

Stability analysis by ELISA samples of SpeAB in tris at pH 8 were prepared with either 10% sucrose or 10% mannitol and stored at 45° C. for 9 days. Samples were taken at day 0, 1, and 9 for analysis. ELISA samples were diluted 25 fold in coating buffer (20 mM tris, 150 mM NaCl, pH 9) and 100 µl was placed in duplicate in the appropriate well of a 96 well plate. Standards were prepared by performing six, 2-fold serial dilutions starting at 4 µg/ml in the appropriate wells of the plate. The plate was incubated for 1 hour at 37° C. and then washed 3 times with 100 µl/well of washing buffer (20 mM $PO_4$, 150 mM NaCl, pH 7.4). Next, 100 µl/well of blocking buffer (100 µg/ml BSA, 20 mM $PO_4$, 150 mM NaCl, pH 7.4) was added to the plate and the plate was incubated for 1 hour at 37° C. The plate was washed as before and 100 µl/well of a 1:25,000 dilution of rat anti-SpeAB antisera was added to the plate and the plate was incubated for 1 hour at 37° C. The plate was washed as before and 100 µl/well of a 1:70,000 dilution of goat anti-rat IgG-HRP was added to the plate and the plate was incubated for 1 hour at 37° C. The plate was washed as before and 100 µl/well of TMB reagent was added to the plate and the plate was incubated for 20 minutes at room temperature. The reaction was stopped by addition of 100 µl/well 3 M $H_2SO_4$ and the absorbance of the wells was monitored at 450 nm. The concentration of SpeAB in each sample was determined by calculation from the standard curve. The data demonstrate that both sucrose and mannitol significantly enhance the stability of SpeAB in solution. Nearly all of the SpeAB remained intact after 9 days of storage at 45° C. with the sucrose or mannitol while only 20% of SpeAB in Tris buffer remained (FIG. 5).

Example 3

Adsorption Studies

An adsorbed formulation (>80%) and a non-adsorbed formulation (<20%) of SpeAB was produced for comparison in animal potency studies. Therefore, a SpeAB formulation was produced having 10% sucrose stabilizer in which both 0.025 (adsorbed) and 1 (non-absorbed) molar ratio phosphate treated aluminum hydroxide adjuvant were used. The data demonstrated that the added stabilizer had an impact on the non-adsorbed formulation with the 1:1 molar ratio of phosphate treatment. The adsorption in that formulation increased to 69% which is well above the target of <20% adsorbed (FIG. 6). The adsorbed formulation had a value of 87% SpeAB adsorbed which was in the target range of >80% adsorbed. To achieve the target adsorption level for the non-adsorbed formulation the study was repeated and phosphate to aluminum treatment ratios of 1.5:1 and 2:1 were included (FIG. 7). The results show that a 2:1 ratio of phosphate treated aluminum hydroxide adjuvant achieves <20% adsorption in the presence of 10% sucrose. Based on the data a phosphate treatment ratio of 0.025 was used for the adsorbed formulation and a phosphate treatment ratio of 2 was used for the non-adsorbed formulation in the potency study (Example 4).

Example 4

In Vivo Potency Studies

A potency study in mice was performed. The formulations produced for the potency study are presented in Table 2. Candidate formulation 13VF001 was the antigen only control. 13VF002 and 13VF003 were adjuvant only controls. 13VF004-13VF006 were the adsorbed formulations and 13VF007-13VF009 were the non-adsorbed formulations. Animals were administered 100 μl of vaccine, IM on days 0 and 14. Characterization testing was performed on days 0 and 14 and sera samples were obtained on days 14 and 28 to determine the immune response.

TABLE 2

Formulations produced for assessing potency of SpeAB in mice

| Group | Formulation | Total (ml) |
|---|---|---|
| 13VF001 | 50 μg/ml SpeAB, 20 mM Tris, 10% sucrose, pH 8 | 3.3 |
| 13VF002 | 1.7 mg/ml AHP1, 20 mM Tris, 10% sucrose, pH 8 | 3.3 |
| 13VF003 | 1.7 mg/ml AHP2, 20 mM Tris, 10% sucrose, pH 9 | 3.3 |
| 13VF004 | 50 μg/ml SpeAB, 1.7 mg/ml AHP1, 20 mM 8 Tris, 10% sucrose, pH | 3.3 |
| 13VF005 | 20 μg/ml SpeAB, 1.7 mg/ml AHP1, 20 mM Tris, 10% sucrose, pH 8 | 3.3 |
| 13VF006 | 4 μg/ml SpeAB, 1.7 mg/ml AHP1, 20 mM Tris, 10% sucrose, pH 8 | 3.3 |
| 13VF007 | 50 μg/ml SpeAB, 1.7 mg/ml AHP2, 20 mM Tris, 10% sucrose, pH 8 | 3.3 |
| 13VF008 | 20 μg/ml SpeAB, 1.7 mg/ml AHP2, 20 mM Tris, 10% sucrose, pH 8 | 3.3 |
| 13VF009 | 4 μg/ml SpeAB, 1.7 mg/ml AHP2, 20 mM Tris, 10% sucrose, pH 8 | 3.3 |

AHP1 is aluminum hydroxide adjuvant with a ratio of phosphate to aluminum ratio of 2:1, whereas AHP2 is aluminum hydroxide adjuvant with a ratio of phosphate to aluminum ratio of 0.025:1.

The results of the characterization testing demonstrate that the formulations met all of their targets immediately following production and there were no significant changes during storage at 2-8° C. for 14 days (Table 3). Testing was not performed on the adjuvant only controls, 13VF002 and 13VF003.

TABLE 3

Characterization testing of potency study formulations

| Formulation | Assay | Target | Result Day 0 | Result Day 14 |
|---|---|---|---|---|
| 13VF001 | Visual Inspection | Clear, colorless solution free of particulates | Conforms | Conforms |
| | pH | 7.5-8.5 | 8.15 | 8.18 |
| | Total Protein | 40-60 μg/ml | 48 μg/ml | 42 μg/ml |
| | Endotoxin | <100 EU/ml | 31 EU/ml | N/A |
| 13VF004 | Visual Inspection | Homogeneous suspension of white particles | Conforms | Conforms |
| | pH | 7.5-8.5 | 8.33 | 8.32 |
| | % Adsorbed | >80% | 100% | 96% |

TABLE 3-continued Characterization testing of potency study formulations

| Formulation | Assay | Target | Result Day 0 | Day 14 |
|---|---|---|---|---|
| 13VF005 | Visual Inspection | Homogeneous suspension of white particles | Conforms | Conforms |
| | pH | 7.5-8.5 | 8.34 | 8.22 |
| | % Adsorbed | >80% | 100% | 98% |
| 13VF006 | Visual Inspection | Homogeneous suspension of white particles | Conforms | Conforms |
| | pH | 7.5-8.5 | 8.34 | 8.27 |
| | % Adsorbed | >80% | 100% | 100% |
| 13VF007 | Visual Inspection | Homogeneous suspension of white particles | Conforms | Conforms |
| | pH | 7.5-8.5 | 7.99 | 8.01 |
| | % Adsorbed | <20% | 19% | 19% |
| 13VF008 | Visual Inspection | Homogeneous suspension of white particles | Conforms | Conforms |
| | pH | 7.5-8.5 | 8.04 | 8.06 |
| | % Adsorbed | <20% | 13% | 17% |
| 13VF009 | Visual Inspection | Homogeneous suspension of white particles | Conforms | Conforms |
| | pH | 7.5-8.5 | 8.01 | 8.02 |
| | % Adsorbed | <20% | 0% | 0% |

SpeAB IgG Titer

Ninety-six well plates were coated overnight at 4° C. with 100 µL of 10 µg/mL SpeAB in 0.1 M carbonate buffer at pH 9.6. The coating solution was removed and the plates were washed three times with 0.05% Tween in PBS (PBS-T). The plates were blocked with 200 µl of 1% (w/v) BSA/PBS-T per well for one hour at 37° C. After three times of washes with 0.05% Tween in PBS, wells were incubated with serial dilutions of serum samples in blocking buffer in triplicate and incubated for two hours at 37° C. The plates were washed and 100 µL of 1:5000 diluted peroxidase-conjugated goat anti-mouse IgG (Sigma, St. Louis, Mo.) was added to each well. The plates were washed and each well received 100 µl 3,3',5,5' tetramethylbenzidine (TMB; Sigma). After incubation in the dark at room temperature for 20 min, 50 µL of 2 M sulfuric acid was added to stop the reaction. The absorbance was read at 450 nm in a BioTEK synergy HT microplate reader (BioTEK, Winooski, Vt.). Titers were calculated as the dilution at which the OD reading reached 0.2.

Neutralizing Antibodies

Mouse serum samples were heat-inactivated for 30 minutes at 56° C. They were diluted to 1:25 and incubated for 1 h at 37° C. with SpeA (Toxin Technology, Sarasota, Fla.) at 80 ng/mL. Human PBMC (Zen-bio, Research Triangle Park, N.C.) were diluted to $2\times10^6$ cells/mL in RPMI1640 supplemented with 10% fetal calf serum 100 U/ml penicillin, 100 µg/ml streptomycin, and 0.25 µg/ml amphotericin B and added to the wells of a 96 well plate at 100 µL/well. Triplicate wells 20 ng/mL SpeA (positive control), medium only (negative control), or 20 ng/mL mixed with mouse serum. After 48 h incubation at 37° C./5% CO2, the supernatants were collected and analyzed by ELISA for the concentration of IFNγ. The neutralizing activity was calculated as 100−(IFNγ sample/IFNγ control)×100.

Statistical Analysis

Figure 8A:
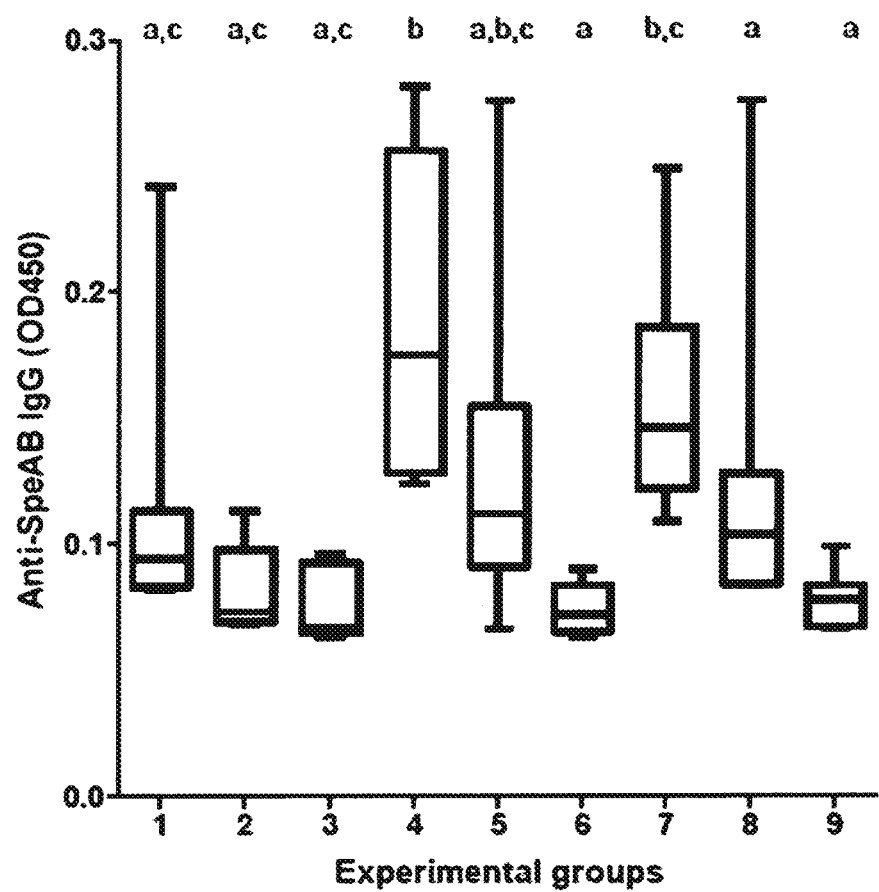
Figure 9:
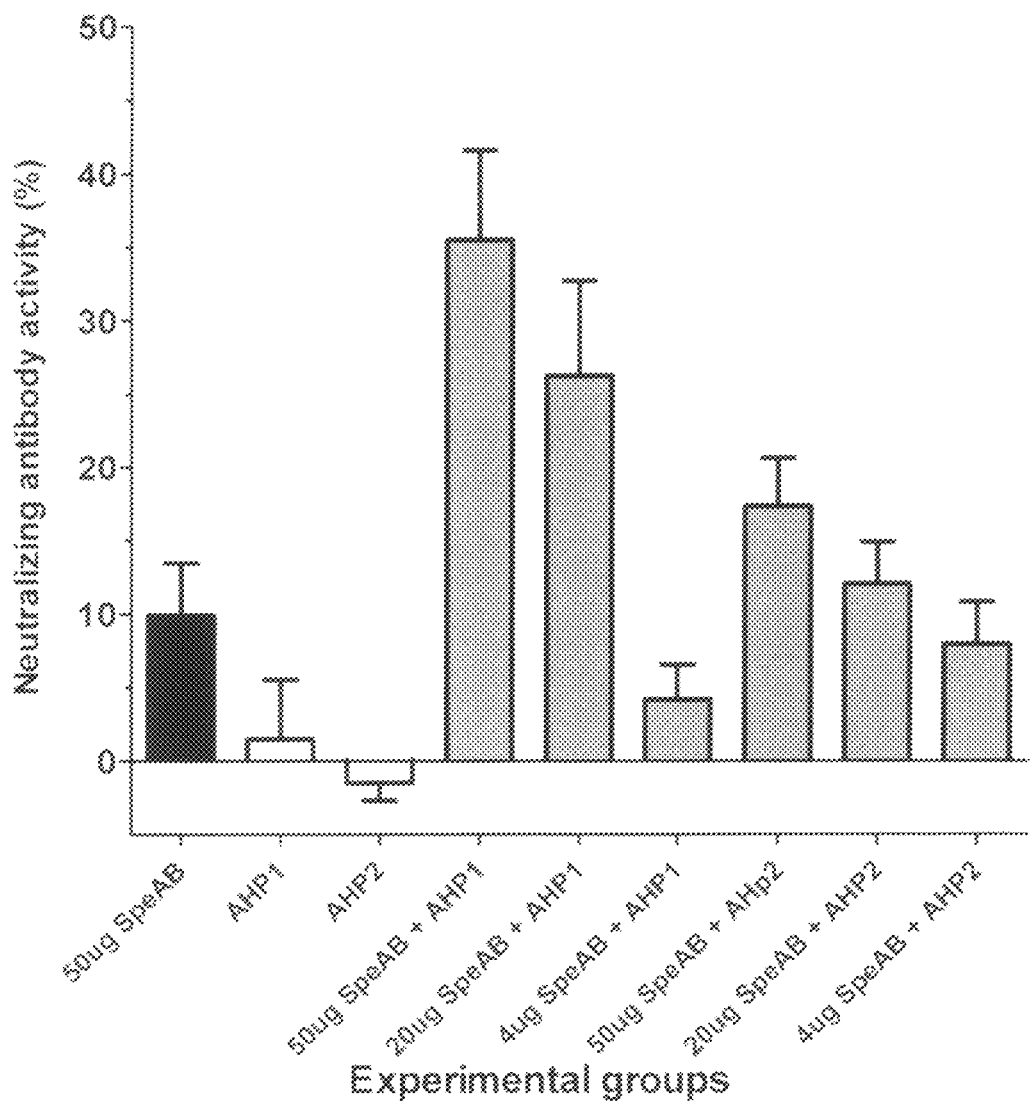
FIG. 9 shows neutralization of SpeA by antisera from mice in the potency study.
Figure 10:
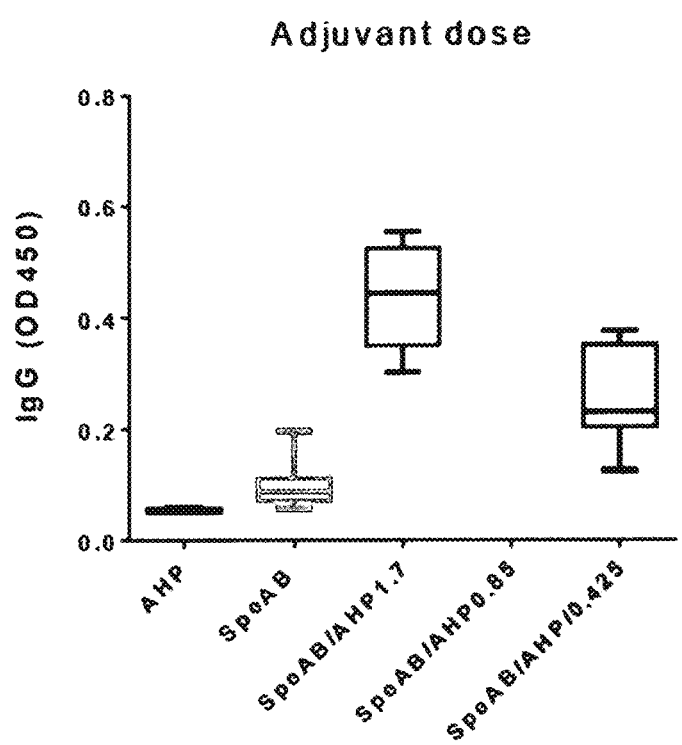
FIG. 10 shows the responses obtained in various formulations with varying adjuvant concentrations.

The anti-SpeA IgG titers are presented as the box and whisker plots with the median, 5-95% confidence interval (box) and range (whiskers). To determine if the differences between groups were statistically different, log-transformed titers were analyzed by one-way ANOVA with post-hoc analysis by Tukey's multiple comparison test. Differences were considered significant at p<0.05. The neutralizing activity is presented as the mean+SEM. The statistical significance of differences of the group means was determined by one-way ANOVA with post-hoc analysis by Tukey's multiple comparison test. Differences were considered significant at p<0.05. Antigen specific total IgG was determined at both day 14 and day 28 (FIG. 8A and FIG. 8B). The data shows that by day 14 after the primary vaccine administration mice given formulation 13VF004 had already achieved a significantly greater level of antigen specific antibody than antigen only and adjuvant only controls. The dose response in the adjuvanted formulations was also apparent at day 14. By day 28 the mice administered 13VF004 had a significantly greater titer than all other groups in the study. This demonstrates the aluminum adjuvant does enhance the immunogenicity of SpeAB.

Determination of whether the antibodies produced were functional at neutralizing the toxicity of wild type SpeA was performed utilizing an assay monitoring neutralization of SpeA toxin. SpeA was first mixed with sera from each group in the potency study. The mixture was then combined with peripheral blood mononuclear cells (PBMCs) and incubated for 12 hours. Following incubation the level of interferon-γ (INF-γ) produced by the PBMCs was determined by ELISA. Since SpeA is a superantigen it is able to crosslink the MHC II molecules on antigen presenting cells with the T-cell receptor on T-cells causing production of INF-γ. Therefore, binding of the toxin by neutralizing antibodies would cause a decrease in the level of INF-γ produced. The data is in agreement with the total IgG analysis in that sera from the group administered 13VF004 had the highest level of toxin neutralization which resulted in a decrease in the amount of INF-γ produced by the PBMCs (FIG. 9).

Example 5

Atmospheric Spray Freeze Drying SpeAB

Atmospheric spray freeze drying of bulk SpeAB drug substance was investigated as a method for producing stable SpeAB. SpeAB in 20 mM Tris, 10% sucrose at pH 8 was atomized using an ultrasonic nozzle, frozen in an ultralow temperature environment, and dried with nitrogen gas at a primary temperature of −40° C., secondary drying at a temperature of −15° C. and final drying at −5° C. Once dried, the powder was raised to room temperature to stabilize and thus harvested. For optimization of the drying cycle the $T_g'$ of the SpeAB bulk drug substance was determined by differential scanning calorimetry.

TABLE 4

| Summary of Tg' SpeAB Analysis | | | |
|---|---|---|---|
| Sample # | Tg' Onset (° C.) | Tg' Midpoint (° C.) | Tg' Endpoint (° C.) |
| 1 | −36.38 | −34.78 | −33.33 |
| 2 | −37.03 | −35.28 | −34.00 |
| 3 | −36.85 | −35.42 | −33.89 |
| Average | −36.75 | −35.16 | −33.74 |

For this determination a Q 2000 TA MDSC instrument was used to obtain these measurements. The DSC was run in the Standard Ramp mode. The DSC was chilled to −90° C. prior to the experiment. Next, 15 μL of SpeAB sample was pipetted and sealed into an Aluminum Hermetic pan. This pan was then submersed in liquid nitrogen for a minute. After the pan had been frozen, it was placed into the DSC which monitored the heat flow from (−90° C.) to 25° C. The temperature was increased at a ramp rate of 10° C./min.

Using the optimized drying parameters the SpeAB powder was produced and then characterized by scanning electron microscopy, residual moisture, differential scanning calorimetry, size exclusion chromatography, particle sizing by laser diffraction. The scanning electron microscope image of the SpeAB powder indicated that spherical particles with some porous nature were produced.

The particle size of the SpeAB powder was determined by laser diffraction. From this it was determined that the mean particle size for the powder was approximately 53 μm.

TABLE 5

| Particle size of SpeAB powders determined by laser diffraction | | | |
|---|---|---|---|
| Run | ×10 (μm) | ×50 (μm) | ×90 (μm) |
| 1 | 26.90 | 50.95 | 89.05 |
| 2 | 29.24 | 54.88 | 95.57 |
| Average | 28.07 | 52.92 | 92.31 |

The residual moisture was then determined by Karl Fisher titration. (Table 6). It was determined that the residual moisture in the powder was about 2.65%.

TABLE 6

| Residual moisture of SpeAB powder determined by Karl Fisher titration | |
|---|---|
| Run | Residual Moisture (%) |
| 1 | 2.16 |
| 2 | 2.65 |
| 3 | 3.15 |
| Average | 2.65 |

The glass transition temperature, $T_g$, of the SpeAB powder was determined by modulated DSC with a temperature range of −25° to 70° C. and a ramp rate of 1° C./min. The onset $T_g$ for the powder was determined to be 30.24° C.

Finally, the recovery of SpeAB following the ASFD processing was evaluated by SEC-HPLC. The concentration of the SpeAB stock was determined to be 0.625+0.04 mg/ml by BCA assay. After the ASFD process, the powder obtained was analyzed for SpeAB content by weighing and reconstituting four samples and analyzing them by SEC-HPLC and BCA assay (Table 7). The protein content between these samples did not show significant variability which suggests homogeneous protein distribution throughout the powder. In addition, the structure of the protein is intact after the ASFD process since the recovery by BCA assay was 95+6% while by SEC-HPLC was 89+1%.

TABLE 7

| SpeAB recovered in the powder after the ASFD process | | |
|---|---|---|
| Sample # | % SpeAB by BCA | % SpeAB by HPLC |
| 1 | 99 | 87 |
| 2 | 101 | 90 |
| 3 | 93 | 89 |
| 4 | 88 | 89 |

SEM of this solid showed an amorphous structure which contained remnants of the SpeAB proteins in a non-uniform concentration as demonstrated by both BCA assay and HPLC analysis. Furthermore, these analytical methodologies were complimentary, for accessing the viability of the analyte following the ASFD process, was documented. The content of SpeAB protein in the ASFD powders demonstrates that this drying methodology is not detrimental to this protein as demonstrated by SEC-HPLC.

Example 6

Varied Amounts of Al Adjuvant

In this example vaccines were prepared in which the aluminum adjuvant concentration was varied from 1.7, 0.85, to 0.425 mg Al/mL. Prior to administration in mice formulations were evaluated by Aspect, pH, and adsorption (Table 8). All formulations met the specification targets for each parameter.

TABLE 8

| Formulations with varying amounts of aluminum adjuvant were monitored by aspect, pH, and adsorption prior to administration to mice | | | |
|---|---|---|---|
| Group | Assay | d0 | d14 |
| Antigen only | Aspect | Conforms | Conforms |
| | pH | 7.99 | 8.00 |
| SpeAB 1.7 mg/ml | Aspect | Conforms | Conforms |
| AHP | pH | 8.02 | 8.04 |
| | Adsorption | 100% | 94% |
| SpeAB 0.85 mg/ml | Aspect | Conforms | Conforms |
| AHP | pH | 7.97 | 8.04 |
| | Adsorption | 100% | 96% |
| SpeAB 0.425 mg/ml | Aspect | Conforms | Conforms |
| AHP | pH | 7.97 | 8.04 |
| | Adsorption | 91% | 94% |

Briefly, Balb/c mice were administered vaccine on days 0 and 14. Serum was obtained on day 28 and evaluated for the presence of antigen specific IgG. (FIG. 10). The data demonstrates equivalent immune responses were obtained down to an adjuvant concentration of 0.85 mg Al/mL. However, once the adjuvant was diluted to 0.425 mg Al/mL there was a significant decrease in antibody response.

The invention claimed is:

1. A stable immunological composition comprising:

(a) 20 to 100 micrograms per ml of a genetically engineered recombinant SpeAB fusion protein comprising *Streptococcus pyogenes* pyrogenic exotoxin A (SpeA) that is fused to *Streptococcus pyogenes* pyrogenic exotoxin B (SpeB);

(b) 0.5 to 1.7 milligrams per ml of aluminum salt;

(c) 2 to 10% of the stabilizer sucrose; and (d) phosphate, wherein the ratio of the phosphate to the aluminum salt is between 0.025:1 to 1:1.

2. The immunological composition of claim 1, wherein the pH of the composition is from about 7.5 to about 8.5.

3. The immunological composition of claim 1 further comprising 10 to 50 mM Tris.

4. The immunological composition of claim 1, wherein the SpeAB fusion protein is adsorbed to the aluminum salt.

5. The immunological composition of claim 1, wherein the SpeAB fusion protein is at least 80% adsorbed to the aluminum salt.

6. The immunological composition of claim 1, wherein the SpeAB fusion protein is at least than 20% adsorbed to the aluminum salt.

* * * * *